United States Patent
Marion et al.

(10) Patent No.: US 11,591,543 B2
(45) Date of Patent: Feb. 28, 2023

(54) AROMA CHEMICAL COMPOSITIONS CONTAINING 3,5-DIETHYL-2-PROPYL-TETRAHYDROPYRAN AND/OR UNSATURATED DERIVATIVES THEREOF

(71) Applicant: BASF SE, Ludwigshafen am Rhein (DE)

(72) Inventors: Nicolas Marion, Saint-Louis (FR); Rolf Pinkos, Ludwigshafen am Rhein (DE); Stefan Ruedenauer, Lampertheim (DE); Florian Garlichs, Lampertheim (DE); Ralf Pelzer, Lampertheim (DE); Roman Dostalek, Ludwigshafen am Rhein (DE); Joachim Pfeffinger, Ludwigshafen am Rhein (DE); Anja Vinckier, Antwerp (BE); Stephanie Renz, Ludwigshafen am Rhein (DE); Christoph Stock, Ludwigshafen am Rhein (DE); Regina-Margareta Berg, Ludwigshafen am Rhein (DE); Miriam Bru Roig, Ludwigshafen am Rhein (DE); Margarethe Klos, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 342 days.

(21) Appl. No.: 16/753,413

(22) PCT Filed: Oct. 5, 2018

(86) PCT No.: PCT/EP2018/077112
§ 371 (c)(1),
(2) Date: Apr. 3, 2020

(87) PCT Pub. No.: WO2019/068856
PCT Pub. Date: Apr. 11, 2019

(65) Prior Publication Data
US 2021/0403826 A1 Dec. 30, 2021

(30) Foreign Application Priority Data
Oct. 5, 2017 (EP) .................. 17194908

(51) Int. Cl.
*C11B 9/00* (2006.01)
*C07D 309/04* (2006.01)

(52) U.S. Cl.
CPC ............ *C11B 9/008* (2013.01); *C07D 309/04* (2013.01)

(58) Field of Classification Search
CPC ..................................... C11B 9/008
See application file for complete search history.

(56) References Cited

U.S. PATENT DOCUMENTS

| | | |
|---|---|---|
| 3,903,171 A | 9/1975 | Toussaint et al. |
| 5,756,856 A | 5/1998 | Bueschken et al. |
| 6,765,119 B2 | 7/2004 | Hoffmann et al. |
| 8,242,289 B2 | 8/2012 | Oertling et al. |
| 9,994,540 B2 | 6/2018 | Rüdenauer et al. |
| 2008/0242899 A1 | 10/2008 | Oota et al. |
| 2010/0226864 A1* | 9/2010 | Oertling .................. A61P 43/00 424/59 |
| 2013/0258467 A1* | 10/2013 | Shiraiwa .................. C09D 4/00 359/483.01 |
| 2016/0340292 A1* | 11/2016 | Ruppin .................... C08K 5/06 |

FOREIGN PATENT DOCUMENTS

| | | |
|---|---|---|
| DE | 2008128 A1 | 9/1971 |
| DE | 2628987 A1 | 1/1978 |
| DE | 10024542 A1 | 11/2001 |
| EP | 2168957 A2 | 3/2010 |
| GB | 1579159 A | 11/1980 |
| WO | WO-2015148743 A1 | 10/2015 |
| WO | WO-2015158584 A1 | 10/2015 |

OTHER PUBLICATIONS

Eliel, E., et al., "Carbon-13 NMR Spectra of Saturated Heterocycles", Organic Magnetic Resonance, vol. 21, No. 2, (1983), pp. 94-107.
International Search Report for PCT/EP2018/077112 dated Nov. 7, 2018.
Kula, J., et al., "Tetrahydrofuran and Tetrahydropyran Derivatives as Odor Substances", Perfumer & Flavorist, vol. 17, No. 1, (1992), pp. 77-92.

(Continued)

*Primary Examiner* — Arrie L Reuther
(74) *Attorney, Agent, or Firm* — Faegre Drinker Biddle & Reath LLP

(57) ABSTRACT

The present invention relates to aroma chemical compositions containing 3,5-diethyl-2-propyl-tetrahydropyran, a 3,5-diethyl-2-propyl-dihydropyran or a 3,5-diethyl-2-propyl-pyran, a mixture of such compounds, a stereoisomer of one of these compounds, or a mixture of stereoisomers of one or more of these compounds. The invention further relates to a method for preparing such compounds, stereoisomers or mixtures thereof, to the composition obtainable by this method, to the use of such compounds as an aroma chemical or for modifying the scent character of a fragranced composition; and to a method for preparing a fragranced composition or for modifying the scent character of a fragranced composition using said compounds. Moreover, the invention relates to 3,5-diethyl-2-propyl-tetrahydropyran, to its stereoisomers and to mixtures of these stereoisomers.

18 Claims, No Drawings

(56) References Cited

OTHER PUBLICATIONS

Von Wittko, F., et al., "Alkylsubstituierte 3,4-Dihydro-2H-pyrane: Massenspektrometrie, Synthese und Identifizierung als Insekteninhaltsstoffe", Angewandte Chemie, vol. 94, No. 9, (1982), pp. 704-706 (in German).
Written Opinion of the International Searching Authority for PCT/EP2018/077112 dated Nov. 7, 2018.

* cited by examiner

AROMA CHEMICAL COMPOSITIONS CONTAINING 3,5-DIETHYL-2-PROPYL-TETRAHYDROPYRAN AND/OR UNSATURATED DERIVATIVES THEREOF

CROSS-REFERENCE TO RELATED APPLICATIONS

This application is a national stage application (under 35 U.S.C. § 371) of PCT/EP2018/077112, filed Oct. 5, 2018, which claims benefit of European Application No. 17194908.4, filed Oct. 5, 2017, both of which are incorporated herein by reference in their entirety.

The present invention relates to aroma chemical compositions containing 3,5-diethyl-2-propyl-tetrahydropyran, a 3,5-diethyl-2-propyl-dihydropyran or a 3,5-diethyl-2-propyl-pyran, or containing a mixture of such compounds, or containing a stereoisomer of one of these compounds, or a containing a mixture of stereoisomers of one or more of these compounds. The invention further relates to a method for preparing such compounds, stereoisomers or mixtures thereof, to the composition obtainable by this method, to the use of such compounds, stereoisomers or mixtures thereof as an aroma chemical, to the use of such compounds, stereoisomers or mixtures thereof for modifying the scent character of a fragranced composition; and to a method for preparing a fragranced composition or for modifying the scent character of a fragranced composition using said compounds, mixtures, stereoisomers or stereoisomer mixtures. Moreover, the invention relates to 3,5-diethyl-2-propyl-tetrahydropyran, to its stereoisomers and to mixtures of these stereoisomers.

TECHNICAL BACKGROUND

Despite a large number of existing aroma chemicals (fragrances and flavorings), there is a constant need for new components in order to be able to satisfy the multitude of properties desired for extremely diverse areas of application. These include, firstly, the organoleptic properties, i.e. the compounds should have advantageous odiferous (olfactory) or gustatory properties. Furthermore, aroma chemicals should also have additional positive secondary properties, such as e.g. an efficient preparation method, the possibility of providing better sensory profiles as a result of synergistic effects with other fragrances, a higher stability under certain application conditions, a higher extendability, a better staying power, etc.

However, since even small changes in chemical structure bring about massive changes in the sensory properties such as odor and also taste, the targeted search for substances with certain sensory properties such as a certain odor is extremely difficult. The search for new fragrances and flavorings is therefore in most cases difficult and laborious without knowing whether a substance with the desired odor and/or taste will even actually be found.

Moreover, as a result of the predictable exhaustion of fossil fuels and the desire to reduce waste, also in the form of exhaust gases, it has become of ever increasing importance to maximize the efficiency of industrial production processes and at the same time to make a more reasonable use of unavoidable organic side products than just using them as a fuel or combustion material, as is presently done in most cases. Even if this fueling/combustion is used for the production of energy and thus serves at least a purpose, this use is not satisfactory, as it wastes potentially valuable materials.

EP-A-2168957 relates to tetrahydropyran compounds which are alkylated or alkenylated in the 2- and 3-positions and may moreover be alkylated or alkenylated in 6-position, relative to the 1-position of the oxygen ring atom. The compounds are said to be useful as aroma chemicals.

R. N. Mohindru et al. describe in Pafai Journal, 1984, 15-18 tetrahydropyran compounds carrying in the 2,2,6-positions three methyl groups and in the 6-position another alkyl group or an alkyl-bound phenyl ring. The compounds are said to have interesting odour variations.

J. Kula et al. describe in Perfumer & Flavorist, 1992, 17, 77-92 the synthesis of various tetrahydropyran derivatives as odour substances.

US 2008/0242899 relates to a process for preparing purified alcohols by subjecting an aldehyde to an aldol condensation, hydrogenating the condensate to give a crude alcohol and distilling the crude alcohol to give a pure alcohol. The pure alcohol is to give satisfactory results in a sulfuric acid coloring test. For achieving this goal, the crude alcohol subjected to the distillation step is required to contain oxygenic heterocycles bearing carbon-carbon double bonds in the cycle in an amount of as low as 200 ppm by weight or less. The aldehyde is in particular n-butyraldehyde, the condensate being thus 2-ethylhexenal and the alcohol 2-ethylhexanol. In this case, the undesired heterocycles formed as by-products in the aldol condensation step and the concentration of which is to be at most 200 ppm in the crude alcohol composition are 3,5-diethyl-2-propyl-pyran and 3,5-diethyl-2-propyl-dihydropyran. One way of reducing the amount of the pyran and the dihydropyran components is said to be their hydrogenation to the corresponding tetrahydropyran. This corresponding tetrahydropyran is however neither isolated nor characterized nor connected with any property (except for not disturbing the sulfuric acid coloring test), and thus no proof of its formation is given.

It was the object of the present invention to provide new aroma chemicals. These should have pleasant odiferous properties. Furthermore, they should be capable, in combination with other aroma chemicals, of providing novel advantageous sensory profiles. In particular, however, these should be available from undesired by-products of industrial processes which otherwise would be discarded or brought to a low-value use, such as the production of energy.

This object is achieved by the compound of formula (I) as shown below (3,5-diethyl-2-propyl-tetrahydropyran, a 3,5-diethyl-2-propyl-dihydropyran or a 3,5-diethyl-2-propyl-pyran), mixtures of different compounds I, a stereoisomer of such a compound, or mixtures of stereoisomers of such a compound I or of different compounds 1. These compound are available from the production of 2-ethylhexanal from 2-ethylhexenal and also from the production of 2-ethylhexanol from 2-ethylhexenal.

SUMMARY OF THE INVENTION

It was found that the compounds of the formula (I) as described below, mixtures thereof, stereoisomers thereof and mixtures of stereoisomers thereof exhibit a pleasant and characteristic odor and can be used to produce fragranced compositions. In addition, they can advantageously be combined with other aroma chemicals to create new scent profiles.

Accordingly, the invention relates to an aroma chemical composition, comprising a compound of formula (I)

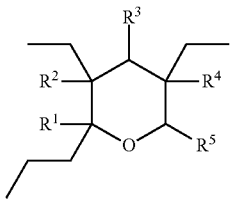

(I)

wherein $R^1$, $R^2$, $R^3$, $R^4$ and $R^5$ are hydrogen; or $R^1$ and $R^2$, together with the carbon atoms to which they are bound, form a C—C double bond and $R^3$, $R^4$ and $R^5$ are hydrogen; or $R^2$ and $R^3$, together with the carbon atoms to which they are bound, form a C—C double bond and $R^1$, $R^4$ and $R^5$ are hydrogen; or $R^3$ and $R^4$, together with the carbon atoms to which they are bound, form a C—C double bond and $R^1$, $R^2$ and $R^5$ are hydrogen; or $R^4$ and $R^5$, together with the carbon atoms to which they are bound, form a C—C double bond and $R^1$, $R^2$ and $R^3$ are hydrogen; or $R^1$ and $R^2$, together with the carbon atoms to which they are bound, form a C—C double bond, $R^3$ and $R^4$, together with the carbon atoms to which they are bound, form a C—C double bond, and $R^5$ is hydrogen; or $R^1$ and $R^2$, together with the carbon atoms to which they are bound, form a C—C double bond, $R^4$ and $R^5$, together with the carbon atoms to which they are bound, form a C—C double bond, and $R^3$ is hydrogen; or $R^2$ and $R^3$, together with the carbon atoms to which they are bound, form a C—C double bond, $R^4$ and $R^5$, together with the carbon atoms to which they are bound, form a C—C double bond, and $R^1$ is hydrogen;

or a stereoisomer thereof, or a mixture of different compounds of formula (I), or a mixture of stereoisomers of a compound of formula (I) or of different compounds of formula (I).

The aroma chemical composition comprises at least one further component. This further component is generally selected from the group consisting of one or more other aroma chemicals different from compounds I and at least one non-aroma component.

The at least one non-aroma component has no or no noteworthy olfactory or flavor properties. The non-aroma component generally serves for the dilution and/or the fixing of the aroma chemical(s). It can be liquid or oil-like as well as wax-like or solid.

The non-aroma component is preferably selected from the group consisting of surfactants, oil components and solvents.

Another aspect of the invention is the use of a compound (I) or of a stereoisomer thereof or of a mixture of different compounds of formula (I), or of a mixture of stereoisomers of a compound of formula (I) or of different compounds of formula (I) as aroma chemicals. Yet another aspect is the use of a compound (I) or of a stereoisomer thereof or of a mixture of different compounds of formula (I), or of a mixture of stereoisomers of a compound of formula (I) or of different compounds of formula (I) for modifying the scent character of a fragranced composition.

The invention further relates to a method for preparing compounds (I) or mixtures of different compounds (I) or a stereoisomer thereof or mixtures of stereoisomers of a compound of formula (I) or of different compounds of formula (I); to a composition obtainable by this method, to the use of this composition as an aroma chemical, and to an aroma chemical composition containing this composition.

The invention also relates to the compound of formula (IA)

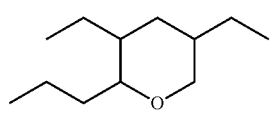

(IA)

and to all stereoisomers thereof, either as single stereoisomers or as a mixture of two or more stereoisomers.

The invention also relates to a method of preparing a fragranced composition, e.g. a fragranced ready-to-use composition, and to a method for modifying the scent character of a fragranced composition, e.g. of a fragranced ready-to-use composition, comprising incorporating the compound of the formula (I) or a mixture of different compounds (I) or a stereoisomer of a compound of the formula (I) or a mixture of stereoisomers of a compound of formula (I) or of different compounds of formula (I) into said composition.

By virtue of their physical properties, the compounds of formula (I) and their stereoisomers have particularly good, virtually universal solvent properties for other fragrances and other customary ingredients in fragranced ready-to-use compositions such as, in particular, perfume compositions. Therefore, the compounds of formula (I), their stereoisomers, their mixtures and mixtures of their stereoisomers are favorably combinable with other aroma chemicals, allowing, in particular, the creation of perfume compositions having novel advantageous sensory profiles.

DETAILED DESCRIPTION OF THE INVENTION

The term "aroma chemical" denotes a substance which is used to obtain a sensory impression, to be more precise an olfactory or flavor impression, in particular a fragrance or flavor impression. The term "olfactory" denotes an odor impression without any positive or negative judgement, while the term "fragrance" (also termed "perfume" or "scent") is connected to an odor impression which is generally felt as pleasant. A flavor induces a taste impression. Preferably, the term "aroma chemical composition", as used herein, refers to a composition which induces a pleasant odor impression.

The term "stereoisomers" encompasses optical isomers, such as enantiomers or diastereomers, the latter existing due to more than one stereogenic center in the molecule, as well as geometrical isomers (cis/trans isomers) as a specific form of diastereomers. For instance, the compounds of the formula (I) wherein $R^1$, $R^2$, $R^3$, $R^4$ and $R^5$ are hydrogen have three stereogenic centers, namely the carbon ring atoms carrying the ethyl groups and the propyl group. The invention provides both the pure enantiomers or diastereomers and mixtures thereof and the use according to the invention of the pure enantiomers or pure diastereomers of the compound (I) or mixtures thereof.

In the terms of the present invention, the term "compound (I)" or "compound of formula (I)", when not defined as a specific stereoisomer or a specific mixture of stereoisomers, refers to an equimolar mixture of all possible configurational stereoisomers. The term is however also used if it is not necessary or not possible to specify in more detail the stereoisomer or mixture of stereoisomers.

In the terms of the present invention, if not specified otherwise, a mixture of stereoisomers is a mixture containing two or more of the possible configurational isomers, which is however not an equimolar mixture of all possible configurational stereoisomers.

Compounds of the formula (I), wherein $R^1$, $R^2$, $R^3$, $R^4$ and $R^5$ are hydrogen, are compounds of the formula (IA).

Compounds of the formula (I), wherein $R^1$ and $R^2$, together with the carbon atoms to which they are bound, form a C—C double bond and $R^3$, $R^4$ and $R^5$ are hydrogen, are compounds of the formula (IB).

Compounds of the formula (I), wherein $R^2$ and $R^3$, together with the carbon atoms to which they are bound, form a C—C double bond and $R^1$, $R^4$ and $R^5$ are hydrogen, are compounds of the formula (IC).

Compounds of the formula (I), wherein $R^3$ and $R^4$, together with the carbon atoms to which they are bound, form a C—C double bond and $R^1$, $R^2$ and $R^5$ are hydrogen, are compounds of the formula (ID).

Compounds of the formula (I), wherein $R^4$ and $R^5$, together with the carbon atoms to which they are bound, form a C—C double bond and $R^1$, $R^2$ and $R^3$ are hydrogen, are compounds of the formula (IE).

Compounds of the formula (I), wherein $R^1$ and $R^2$, together with the carbon atoms to which they are bound, form a C—C double bond, $R^3$ and $R^4$, together with the carbon atoms to which they are bound, form a C—C double bond, and $R^5$ is hydrogen, are compounds of the formula (IF).

Compounds of the formula (I), wherein $R^1$ and $R^2$, together with the carbon atoms to which they are bound, form a C—C double bond, $R^4$ and $R^5$, together with the carbon atoms to which they are bound, form a C—C double bond, and $R^3$ is hydrogen, are compounds of the formula (IG).

Compounds of the formula (I), wherein $R^2$ and $R^3$, together with the carbon atoms to which they are bound, form a C—C double bond, $R^4$ and $R^5$, together with the carbon atoms to which they are bound, form a C—C double bond, and $R^1$ is hydrogen, are compounds of the formula (IH).

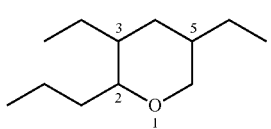
(IA)

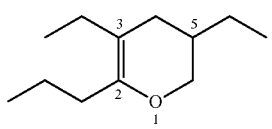
(IB)

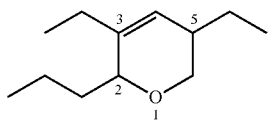
(IC)

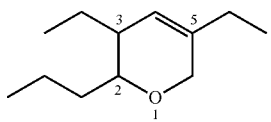
(ID)

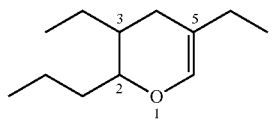
(IE)

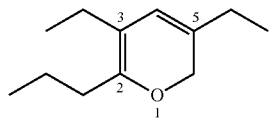
(IF)

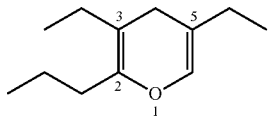
(IG)

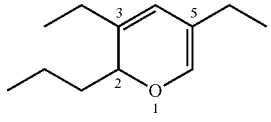
(IH)

The compound (IA) is a tetrahydropyran (to be more precise, it is 3,5-diethyl-2-propyl-tetrahydropyran), the compounds (IB) to (IE) are dihydropyrans (to be more precise a 3,5-diethyl-2-propyl-dihydropyran) and the compounds (IF) to (IH) are pyrans (to be more precise a 3,5-diethyl-2-propyl-pyran).

Preferably, the aroma chemical composition comprises one of the compounds of formula (IA), (IB) or (IE), or a mixture of two or all three of these compounds, or a stereoisomer of a compound of formula (IA), (IB) or (IE); or a mixture of stereoisomers of one of the compounds of formula (IA), (IB) or (IE); or a mixture of stereoisomers of two or all three of the compounds of formula (IA), (IB) and (IE). In particular, the aroma chemical composition comprises the compound of formula (IA); or the compound of formula (IB); or a mixture of the compounds of formula (IA) and (IB); or a stereoisomer of a compound of formula (IA) or (IB); or a mixture of stereoisomers of one of the compounds of formula (IA) or (IB); or a mixture of stereoisomers of the compounds of formula (IA) and (IB).

In a preferred embodiment (embodiment 1), the aroma chemical composition contains the compound of the formula (IA) (i.e. the compound of the formula (I), wherein all of $R^1$, $R^2$, $R^3$, $R^4$ and $R^5$ are hydrogen) or a stereoisomer thereof or a mixture of different stereoisomers thereof.

The compound of formula (IA) has three stereogenic centers and can thus be present in the form of 8 configurational stereoisomers. These are: (2S,3R,5R)-3,5-diethyl-2-propyl-tetrahydropyran, (2S,3S,5R)-3,5-diethyl-2-propyl-tetrahydropyran, (2S,3R,5S)-3,5-diethyl-2-propyl-tetrahydropyran, (2S,3S,5S)-3,5-diethyl-2-propyl-tetrahydropyran, (2R,3S,5S)-3,5-diethyl-2-propyl-tetrahydropyran, (2R,3R,5S)-3,5-diethyl-2-propyl-tetrahydropyran, (2R,3S,5R)-3,5-diethyl-2-propyl-tetrahydropyran and (2R,3R,5R)-3,5-diethyl-2-propyl-tetrahydropyran.

In one embodiment, the compound (IA) is present in the form of one of these stereoisomers or of a mixture of at least two, in particular of 2, 3, 4, 5 or 6, of these stereoisomers.

For obtaining the desired olfactory properties, it is however not necessary to use a specific enantiomer. Therefore, the compound (IA) is generally used in the form of a diastereomer or a mixture of 2, 3 or all 4 diastereomers.

The four possible diastereomers are:
t-3,c-5-diethyl-r-2-propyl-tetrahydropyran (IA.1),
t-3,t-5-diethyl-r-2-propyl-tetrahydropyran (IA.2),
c-3,t-5-diethyl-r-2-propyl-tetrahydropyran (IA.3), and
c-3,c-5-diethyl-r-2-propyl-tetrahydropyran (IA.4), In the above relative nomenclature (see e.g. D. Hellwinkel, Die systematische Nomenklatur der organischen Chemie (The systematic nomenclature in organic chemistry), 4$^{th}$ edition, Springer, Berlin Heidelberg, 1998) the substituent with the highest priority (here propyl) is defined as reference group ("r") and the two ethyl groups are defined relative to this propyl reference group as cis ("c") or trans ("t").

In one preferred embodiment, the aroma chemical composition contains a stereoisomer of the compound of formula (IA), selected from the group consisting of
t-3,c-5-diethyl-r-2-propyl-tetrahydropyran (IA.1),
t-3,t-5-diethyl-r-2-propyl-tetrahydropyran (IA.2),
c-3,t-5-diethyl-r-2-propyl-tetrahydropyran (IA.3), and
c-3,c-5-diethyl-r-2-propyl-tetrahydropyran (IA.4),
or a mixture of two or three or all four of these stereoisomers.

Specifically, the aroma chemical composition contains a mixture of the four following stereoisomers of the compound of formula (IA):
t-3,c-5-diethyl-r-2-propyl-tetrahydropyran (IA.1),
t-3,t-5-diethyl-r-2-propyl-tetrahydropyran (IA.2),
c-3,t-5-diethyl-r-2-propyl-tetrahydropyran (IA.3), and
c-3,c-5-diethyl-r-2-propyl-tetrahydropyran (IA.4),
where in the mixture of the four stereoisomers these are contained in following amounts:
(IA.1): 10 to 25% by weight;
(IA.2): 20 to 35% by weight;
(IA.3): 25 to 40% by weight;
(IA.4): 10 to 32% by weight;
relative to the overall amount of the four stereoisomers (IA.1), (IA.2), (IA.3) and (IA.4) (the amounts of the four stereoisomers add to 100%); where in particular not all four stereoisomers are present in an amount of 25% by weight;
or are contained in following amounts:
(IA.1): 78 to 88% by weight;
(IA.2): 0.5 to 3% by weight;
(IA.3): 5 to 15% by weight;
(IA.4): 2 to 8% by weight;
relative to the overall amount of the four stereoisomers (IA.1), (IA.2), (IA.3) and (IA.4) (the amounts of the four stereoisomers add to 100%).

More specifically, the aroma chemical composition contains a mixture of the four following stereoisomers of the compound of formula (IA):
t-3,c-5-diethyl-r-2-propyl-tetrahydropyran (IA.1),
t-3,t-5-diethyl-r-2-propyl-tetrahydropyran (IA.2),
c-3,t-5-diethyl-r-2-propyl-tetrahydropyran (IA.3), and
c-3,c-5-diethyl-r-2-propyl-tetrahydropyran (IA.4),
where in the mixture of the four stereoisomers these are contained in following amounts:
(IA.1): 12 to 23% by weight;
(IA.2): 24 to 32% by weight;
(IA.3): 30 to 37% by weight;
(IA.4): 12 to 29% by weight;
relative to the overall amount of the four stereoisomers (IA.1), (IA.2), (IA.3) and (IA.4) (the amounts of the four stereoisomers add to 100%);
or are contained in following amounts:
(IA.1): 80 to 85% by weight;
(IA.2): 1 to 2.5% by weight;
(IA.3): 8 to 11% by weight;
(IA.4): 4 to 7% by weight;
relative to the overall amount of the four stereoisomers (IA.1), (IA.2), (IA.3) and (IA.4) (the amounts of the four stereoisomers add to 100%).

In embodiment 1, the aroma chemical composition may contain, in addition to the compound (IA) or a stereoisomer thereof or a mixture of stereoisomers thereof, one or more compounds (IB) to (IH) or one or more stereoisomers thereof. Preferably, however, these are present in minor amounts as compared to the compound (IA), e.g. in an overall amount of at most 30% by weight, preferably at most 20% by weight, more preferably at most 10% by weight, in particular at most 5% by weight, more particularly at most 2% by weight and specifically at most 1% by weight, relative to the total weight of compounds (IA) to (IH). If the composition contains, in addition to the compound (IA) or a stereoisomer thereof or a mixture of stereoisomers thereof, one or more compounds (IB) to (IH), these are in particular compounds (IB), (IE) or mixtures thereof or one or more stereoisomers thereof, and specifically compound (IB) or one or more stereoisomers thereof. In a specific embodiment, the aroma chemical composition of embodiment 1 does not contain any compounds (IB) to (IH).

In an alternatively preferred embodiment (embodiment 2), the aroma chemical composition contains a dihydropyran selected from the group consisting of the compound of the formula (IB), the compound of the formula (IE) and a mixture of the compounds of formulae (IB) and (IE), or contains a stereoisomer of (IB) or (IE) or a mixture of different stereoisomers of (IB) or (IE) or both. Preferably, the aroma chemical composition contains the compound of the formula (IB), optionally in admixture with the compound of the formula (IE), and more preferably the compound (IB).

In embodiment 2, the aroma chemical composition may contain, in addition to the compound (IB) and/or (IE) or one or more stereoisomers thereof, one or more of the compounds (IA), (IC), (ID) and (IF) to (IH) or one or more stereoisomers thereof. Preferably, however, these are present in minor amounts as compared to the compounds (IB) and (IE) or their stereoisomers, e.g. in an overall amount of at most 30% by weight, preferably at most 20% by weight, more preferably at most 10% by weight, in particular at most 5% by weight, more particularly at most 2% by weight and specifically at most 1% by weight, relative to the total weight of compounds (IA) to (IH). If the composition contains one or more compounds (IA), (IC), (ID) and (IF) to (IH), this is in particular the compound (IA) or one or more stereoisomers thereof. Specifically, the aroma chemical composition of embodiment 2 does not contain compounds (IC), (ID) and (IF) to (IH). More specifically, the aroma chemical composition of embodiment 2 does not contain compound (IA), either.

Among embodiments 1 and 2, preference is given to embodiment 1, i.e. to aroma chemical compositions containing the compound (IA) or one or more stereoisomers thereof.

The olfactory properties of the compound (I), of the mixtures of different compounds (I), of the stereoisomers of one or more compounds (I) and of the composition obtainable by the below-described method of the invention, the substance properties (such as solubility in customary solvents and compatibility with further customary constituents of compositions in which aroma chemicals are customarily incorporated) as well as the toxicological acceptability make it/them suitable for the desired use.

Accordingly, as already mentioned above, another aspect of the invention relates to the use of the compound of formula (I) or of a stereoisomer thereof or of a mixture of different compounds (I) or of a mixture of stereoisomers of one or more compounds (I) or of a composition obtainable by the method described below as an aroma chemical.

The below remarks apply both to the aroma chemical composition according to the present invention as well as to the use according to the present invention.

As explained above, the term "aroma chemical" denotes a substance which is used to obtain a sensory impression, to be more precise an olfactory or flavor impression, in particular a fragrance or flavor impression. The term "olfactory" denotes an odor impression without any positive or negative judgement, while the term "fragrance" (also termed "perfume" or "scent") is connected to an odor impression which is generally felt as pleasant. A flavor induces a taste impression.

"Pleasant odor", "pleasant odor impression", "pleasant odiferous properties" are hedonistic expressions which describe the niceness and conciseness of an odor impression conveyed by an aroma chemical. The more general hedonistic expressions "advantageous sensory properties" or "advantageous organoleptic properties" describe the niceness and conciseness of an organoleptic impression conveyed by an aroma chemical. "Niceness" and "conciseness" are terms which are familiar to the person skilled in the art, a perfumer. Niceness generally refers to a spontaneously brought about, positively perceived, pleasant sensory impression. However, "nice" does not have to be synonymous with "sweet". "Nice" can also be the odor of musk or sandalwood. "Conciseness" generally refers to a spontaneously brought about sensory impression which—for the same test panel—brings about a reproducibly identical reminder of something specific. For example, a substance can have an odor which is spontaneously reminiscent of that of an "apple": the odor would then be concisely of "apples". If this apple odor were very pleasant because the odor is reminiscent, for example, of a sweet, fully ripe apple, the odor would be termed "nice". However, the odor of a typically tart apple can also be concise. If both reactions arise upon smelling the substance, in the example thus a nice and concise apple odor, then this substance has particularly advantageous sensory properties.

Preferably, the compound of formula (I) or a stereoisomer thereof, or a mixture of different compounds of formula (I), or a mixture of stereoisomers of a compound of formula (I) or of different compounds of formula (I) or the composition obtainable by the below method of the invention is used as a fragrance.

In particular, the compound of formula (IA) or a stereoisomer thereof or a mixture of different stereoisomers thereof is used to impart a minty, fresh, green, herbal, woody, dried fruits note; or is used to produce a scent with a minty, fresh, green, herbal, woody, dried fruits note.

In particular, the compound of formula (IB) or a stereoisomer thereof or a mixture of different stereoisomers thereof is used to impart a herbal, woody, dried fruits, fatty note; or is used to produce a scent with a herbal, woody, dried fruits, fatty note.

In particular, a mixture of the compounds of formula (IB) and (IE), preferably a ca. 3:1 mixture of the compounds of formula (IB) and (IE), or a stereoisomer thereof or a mixture of different stereoisomers thereof is used to impart a herbal, woody, dried fruits, fatty note; or is used to produce a scent with a herbal, woody, dried fruits, fatty note.

The compound (I) or a stereoisomer thereof or a mixture of different compounds of formula (I) or a mixture of stereoisomers of a compound of formula (I) or of different compounds of formula (I) or the composition obtainable by the below method of the invention is generally used in a ready-to-use composition, to be more specific in a fragranced ready-to-use composition.

Fragranced ready-to-use compositions are for example compositions used in personal care, in home care, in industrial applications as well as compositions used in other applications, such as pharmaceutical compositions or crop protection compositions.

Preferably, the compound of formula (I) or a stereoisomer thereof or a mixture of different compounds of formula (I) or a mixture of stereoisomers of a compound of formula (I) or of different compounds of formula (I) or the composition obtainable by the below method of the invention is used in a composition selected from the group consisting of perfume compositions, body care compositions, hygiene articles, cleaning compositions, textile detergent compositions, compositions for scent dispensers, foods, food supplements, pharmaceutical compositions and crop protection compositions. The compound of formula (I) or the stereoisomer or the mixture of stereoisomers thereof as defined above or the composition obtainable by the above method of the invention is used as an aroma chemical, preferably as a fragrance, in the above compositions.

In particular, the compound of formula (IA) or a stereoisomer or a mixture of different stereoisomers thereof as defined above is used to impart a minty, fresh, green, herbal, woody, dried fruits note to the above-listed compositions.

In particular, the compound of formula (IB) or a stereoisomer thereof or a mixture of different stereoisomers thereof is used to impart a herbal, woody, dried fruits, fatty note to the above-listed compositions.

In particular, a mixture of the compounds of formula (IB) and (IE), preferably a ca. 3:1 mixture of the compounds of formula (IB) and (IE), or a stereoisomer thereof or a mixture of different stereoisomers thereof is used to impart a herbal, woody, dried fruits, fatty note to the above-listed compositions.

Details to the above-listed compositions are given below.

In addition to the olfactory properties, the compound (I), the stereoisomers thereof, the mixtures of different compounds of formula (I) and the composition obtainable by the below method of the invention exhibit advantageous secondary properties.

For example, they can provide better sensory profiles as a result of synergistic effects with other fragrances, which means that they can provide a booster effect for other fragrances. They are therefore suitable as boosters for other fragrances.

Accordingly, another aspect of the invention relates to the use of the compound of formula (I) or of a stereoisomer thereof or of a mixture of different compounds of formula (I) or of a mixture of stereoisomers of a compound of formula (I) or of different compounds of formula (I) or of the composition obtainable by the below method for modifying the scent character of a fragranced composition; and specifically to the use as a booster for other fragrances.

Booster effect means that the substances enhance and intensify in perfumery formulations the overall impression of the mixture. In the mint range, for example, it is known that menthyl methyl ether intensifies the perfumery or taste mixtures of peppermint oils and particularly in top notes brings about a considerably more intensive and more complex perception although the ether itself, being a pure substance, develops no particular intensive odor at all. In fragrance applications, Hedione® (methyl dihydrojasmonate), which as a pure substance only exhibits a light floral jasmin-note, reinforces diffusion, freshness and volume of a perfume composition as an odor booster. Booster effects are particularly desired when top-note-characterized applications are required, in which the odor impression is to be conveyed particularly quickly and intensively, for example in deodorants, air fresheners or in the taste sector in chewing gums.

To achieve such a booster effect, the compounds of the general formula (I) or the stereoisomers thereof are generally used in an overall amount of 0.1-20% by weight, preferably in an overall amount of 0.5 to 5% by weight, in particular in an overall amount of from 0.6 to 3% by weight, based on the total weight of the fragrance mixture. Furthermore, the compound (I), its stereoisomers, the mixture of different compounds of formula (I) or the composition obtainable by the below method of the invention can have further positive effects on the composition in which they are used. For example, they can enhance the overall performance of the composition into which they are incorporated, such as the stability, e.g. the formulation stability, the extendability or the staying power of the composition.

Preferably, the aroma chemical composition comprises
the compound of formula (I), or a stereoisomer thereof, or a mixture of different compounds of formula (I), or a mixture of stereoisomers of a compound of formula (I) or of different compounds of formula (I) or a composition obtainable by the below method of the invention; and at least one further aroma chemical and/or at least one non-aroma component preferably selected from the group consisting of surfactants, oil components and solvents.

The further aroma chemical is of course different from the compound of formula (I) or its stereoisomers or said composition obtainable by the below method of the invention.

By virtue of their physical properties, the compounds of formula (I), their stereoisomers, the mixture of different compounds of formula (I), the mixture of stereoisomers of a compound of formula (I) or of different compounds of formula (I) or the composition obtainable by the below method of the invention have particularly good, virtually universal solvent properties for other fragrances and other customary ingredients in fragranced ready to use compositions such as, in particular, perfume compositions. Therefore, they are well combinable with other aroma chemicals, allowing, in particular, the creation of perfume compositions having novel advantageous sensory profiles. Especially, as already explained above, they can provide a booster effect for other fragrances.

Accordingly, in one preferred embodiment, the aroma chemical composition comprises a compound of formula (I), or a stereoisomer thereof, or a mixture of different compounds of formula (I), or a mixture of stereoisomers of a compound of formula (I) or of different compounds of formula (I) or a composition obtainable by the below method of the invention; and at least one further aroma chemical.

The further aroma chemical can for example be one, preferably 2, 3, 4, 5, 6, 7, 8 or further aroma chemicals, selected from the group consisting of:

Geranyl acetate (3,7-Dimethyl-2,6 octadien-1yl acetate), alpha-hexylcinnamaldehyde, 2-phenoxyethyl isobutyrate (Phenirat[1]), dihydromyrcenol (2,6-dimethyl-7-octen-2-ol), methyl dihydrojasmonate (preferably with a content of cis isomer of more than 60% by weight) (Hedione[9], Hedione HC[9]), 4,6,6,7,8,8-hexamethyl-1,3,4,6,7,8-hexahydro-cyclopenta[g]benzopyran (Galaxolid[3]), tetrahydrolinalool (3,7-dimethyloctan-3-ol), ethyllinalool, benzyl salicylate, 2-methyl-3-(4-tert-butylphenyl)propanal (Lysmeral[2]), cinnamyl alcohol, 4,7-methano-3a,4,5,6,7,7a-hexahydro-5-indenyl acetate and/or 4,7-methano-3a,4,5,6,7,7a-hexahydro-6-indenyl acetate (Herbaflorat[1]), citronellol, citronellyl acetate, tetrahydrogeraniol, vanillin, linalyl acetate, styrolyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthalene (Iso E Super[3]), hexyl salicylate, 4-tert-butylcyclohexyl acetate (Oryclone[1]), 2-tert-butylcyclohexyl acetate (Agrumex HC[1]), alpha-ionone (4-(2,2,6-trimethyl-2-cyclohexen-1-yl)-3-buten-2-one), n-alpha-methylionone, alpha-isomethylionone, alpha-amylcinnamaldehyde, ethylene brassylate, (E)- and/or (Z)-3-methylcyclopentadec-5-enone (Muscenon[9]), 15-pentadec-11-enolide and/or 15-pentadec-12-enolide (Globalide[1]), 15-cyclopentadecanolide (Macrolide[1]), 1-(5,6,7,8-tetrahydro-3,5,5,6,8,8-hexamethyl-2-naphthalenyl)ethanone (Tonalid[10]), 2-isobutyl-4-methyltetrahydro-2H-pyran-4-ol (Florol[9]), 2-ethyl-4-(2,2,3-trimethyl-3-cyclopenten-1-yl)-2-buten-1-ol (Sandolen[1]), cis-3-hexenyl acetate, trans-3-hexenyl acetate, trans-2/cis-6-nonadienol, 2,4-dimethyl-3-cyclohexenecarboxaldehyde (Vertocitral[1]), 2,4,4,7-tetramethyloct-6-en-3-one (Claritone[1]), 2,6-dimethyl-5-hepten-1-al (Melonal[2]), borneol, 3-(3-isopropylphenyl)butanal (Florhydral[2]), 2-methyl-3-(3,4-methylenedioxyphenyl)-propanal (Helional[3]), 3-(4-ethylphenyl)-2,2-dimethylpropanal (Florazon[1]), 7-methyl-2H-1,5-benzodioxepin-3(4H)-one (Calone), 3,3,5-trimethylcyclohexyl acetate (preferably with a content of cis isomers of 70% by weight) or more and 2,5,5-trimethyl-1,2,3,4,4a,5,6,7-octahydronaphthalen-2-ol (Ambrinol S[1]). Within the context of the present invention, the aforementioned aroma chemical(s) are accordingly preferably combined with the compound of formula (I) or a stereoisomer thereof or a mixture of stereoisomers thereof as defined above or a composition obtainable by the method described above.

A further embodiment of the invention relates to a composition comprising a compound of formula (I), or a stereoisomer thereof, or a mixture of different compounds of formula (I), or a mixture of stereoisomers of a compound of formula (I) or of different compounds of formula (I) or a composition obtainable by the below method and at least one further aroma chemical selected from the group consisting of methyl benzoate, benzyl acetate, geranyl acetate, 2-isobutyl-4-methyltetrahydro-2H-pyran-4-ol and linalool.

A further embodiment of the invention relates to a composition comprising a compound of formula (I), or a stereoisomer thereof, or a mixture of different compounds of formula (I), or a mixture of stereoisomers of a compound of formula (I) or of different compounds of formula (I) or a composition obtainable by the below method and 2-isobutyl-4-methyltetrahydro-2H-pyran-4-ol.

A further embodiment of the invention relates to a composition comprising a compound of formula (I), or a stereoisomer thereof, or a mixture of different compounds of formula (I), or a mixture of stereoisomers of a compound of formula (I) or of different compounds of formula (I) or a composition obtainable by the below method and methyl benzoate.

Where trade names are given above, these refer to the following sources:

[1]trade name of Symrise GmbH, Germany;
[2]trade name of BASF SE, Germany;
[3]trade name of International Flavors & Fragrances Inc., USA;
[5]trade name of Danisco Seillans S.A., France;
[9]trade name of Firmenich S.A., Switzerland;
[10]trade name of PFW Aroma Chemicals B.V., the Netherlands.

Further aroma chemicals with which a compound of formula (I), or a stereoisomer thereof, or a mixture of different compounds of formula (I), or a mixture of stereoisomers of a compound of formula (I) or of different compounds of formula (I) or a composition obtainable by the below method can be combined e.g. to give a composition according to the invention can be found e.g. in S. Arctander, Perfume and Flavor Chemicals, Vol. I and II, Montclair, N. J., 1969, self-published or K. Bauer, D. Garbe and H. Surburg, Common Fragrance and Flavor Materials, 4th Ed., Wiley-VCH, Weinheim 2001. Specifically, mention may be made of:

extracts from natural raw materials such as essential oils, concretes, absolutes, resins, resinoids, balsams, tinctures such as e.g.

ambergris tincture; *amyris* oil; *angelica* seed oil; *angelica* root oil; aniseed oil; valerian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calmus oil; camphor oil; *cananga* oil; cardamom oil; cascarilla oil; *cassia* oil; *cassia* absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; Eau de brouts absolute; oak moss absolute; elemi oil; tarragon oil; *eucalyptus citriodora* oil; *eucalyptus* oil; fennel oil; pine needle oil; *galbanum* oil; *galbanum* resin; geranium oil; grapefruit oil; guaiacwood oil; gurjun balsam; gurjun balsam oil; helichrysum absolute; helichrysum oil; ginger oil; iris root absolute; iris root oil; jasmine absolute; calmus oil; camomile oil blue; roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; *litsea cubeba* oil; laurel leaf oil; mace oil; marjoram oil; mandarin oil; *massoia* bark oil; *mimosa* absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; *origanum* oil; palmarosa oil; patchouli oil; *perilla* oil; peru balsam oil; parsley leaf oil; parsley seed oil; petitgrain oil; peppermint oil; pepper oil; pimento oil; pine oil; pennyroyal oil; rose absolute; rose wood oil; rose oil; rosemary oil; Dalmatian sage oil; Spanish sage oil; sandalwood oil; celery seed oil; spike-lavender oil; star anise oil; *styrax* oil; *tagetes* oil; fir needle oil; tea tree oil; turpentine oil; thyme oil; tolubalsam; tonka absolute; tuberose absolute; vanilla extract; violet leaf absolute; *verbena* oil; vetiver oil; juniper berry oil; wine lees oil; wormwood oil; winter green oil; hyssop oil; civet absolute; cinnamon leaf oil; cinnamon bark oil, and fractions thereof, or ingredients isolated therefrom;

individual fragrances from the group of hydrocarbons, such as e.g. 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

the aliphatic alcohols such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; (E/Z)-1-(1-methoxypropoxy)-hex-3-ene; the aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

the aliphatic sulfur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles such as e.g. 2-nonenenitrile; 2-undecenenitrile; 2-tridecenenitrile; 3,12-tridecadienenitrile; 3,7-dimethyl-2,6-octadienenitrile; 3,7-dimethyl-6-octenenitrile; the esters of aliphatic carboxylic acids such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxy acetate; methyl-3,7-dimethyl-2,6-octadienoate; 4-methyl-2-pentyl crotonate;

the acyclic terpene alcohols such as e.g. geraniol; nerol; linalool; lavandulol; nerolidol; farnesol; tetrahydrolinalool; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

the acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranyl acetone; as well as the dimethyl- and diethyl-acetals of geranial, neral, 7-hydroxy-3,7-dimethyloctanal; the cyclic terpene alcohols such as e.g. menthol; isopulegol; alpha-terpineol; terpine-4-ol; menthan-8-ol; menthan-1-ol;

menthan-7-ol; borneol; isoborneol; linalool oxide; nopol; cedrol; ambrinol; vetiverol; guajol; and the formates, acetates, propionates, isobutyrates, butyrates, isovalerates, pentanoates, hexanoates, crotonates, tiglinates and 3-methyl-2-butenoates thereof;

the cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methano-naphthalene-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methyl cedryl ketone);

the cyclic alcohols such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as e.g. alpha-3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers such as e.g. cineol; cedryl methyl ether; cyclododecyl methyl ether; 1,1-dimethoxycyclododecane; (ethoxymethoxy)cyclo-dodecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo-[10.1.0]trideca-4,8-diene; rose oxide; 2-(2,4-dimethyl-3-cyclohexen-1-yl)-5-methyl-5-(1-methylpropyl)-1,3-dioxane;

the cyclic and macrocyclic ketones such as e.g. 4-tert-butylcyclohexanone; 2,2,5-trimethyl-5-pentylcyclopentanone; 2-heptylcyclopentanone; 2-pentylcyclo-pentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopenta-decenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclo-hexadecen-1-one; 7-cyclohexadecen-1-one; (7/8)-cyclohexadecen-1-one; 9-cyclo-heptadecen-1-one; cyclopentadecanone; cyclohexadecanone;

the cycloaliphatic aldehydes such as e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexene carbaldehyde; 4-(4-methyl-3-penten-1-yl)-3-cyclohexenecarbaldehyde; the cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclo-hexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

the esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

the esters of cycloaliphatic alcohols such as e.g. 1-cyclohexylethyl crotonate; the esters of cycloaliphatic carboxylic acids such as e.g. allyl 3-cyclohexylpropionate; allyl cyclohexyloxyacetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexene-carboxylate; ethyl 2-methyl-1,3-dioxolane-2-acetate;

the araliphatic alcohols such as e.g. benzyl alcohol; 1-phenylethyl alcohol, 2-phenylethyl alcohol, 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

the araliphatic ethers such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

the aromatic and araliphatic aldehydes such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-isobutylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxy-benzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones such as e.g. acetophenone; 4-methylacetophenone; 4-methoxyacetophenone; 4-tert-butyl-2,6-dimethylaceto-phenone; 4-phenyl-2-butanone; 4-(4-hydroxyphenyl)-2-butanone; 1-(2-naphthalenyl)-ethanone; 2-benzofuranylethanone; (3-methyl-2-benzofuranyl)ethanone; benzo-phenone; 1,1,2,3,3,6-hexamethyl-5-indanyl methyl ketone; 6-tert-butyl-1,1-dimethyl-4-indanyl methyl ketone; 1-[2,3-dihydro-1,1,2,6- tetramethyl-3-(1-methylethyl)-1H-5-indenyl]ethanone; 5',6', 7',8'-tetrahydro-3',5',5',6',8',8'-hexamethyl-2-acetonaphthone; the aromatic and araliphatic carboxylic acids and esters thereof such as e.g. benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds such as e.g. 2,4,6-trinitro-1,3-dimethyl-5-tert-butylbenzene; 3,5-dinitro-2,6-dimethyl-4-tert-butylacetophenone; cinnamonitrile; 3-methyl-5-phenyl-2-pentenonitrile; 3-methyl-5-phenylpentanonitrile; methyl anthranilate; methyl-N-methylanthranilate; Schiff bases of methyl anthranilate with 7-hydroxy-3,7-dimethyloctanal, 2-methyl-3-(4-tert-butylphenyl) propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3-isopropyl-pyrazine; 2-isobutyl-3-methoxy-pyrazine;

the phenols, phenyl ethers and phenyl esters such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

Advantageous are combinations with aroma chemicals with a sweet note, such as vanillin, 2,5-dimethyl-4-hydroxy-2H-furan-3-one (furaneol) or 3-hydroxy-2-methyl-4H-pyran-4-one (maltol), of the sweet note of which is boosted by the compound (I) or its stereoisomers.

A further embodiment of the invention is directed to a composition comprising the compound of formula (I), or a stereoisomer thereof, or a mixture of different compounds of formula (I), or a mixture of stereoisomers of a compound of formula (I) or of different compounds of formula (I) or a composition obtainable by the below method of the invention and at least one component selected from the group consisting of surfactants, emollients and solvents.

One embodiment of the invention is directed to a composition comprising a compound of formula (I), or a stereoisomer thereof, or a mixture of different compounds of formula (I), or a mixture of stereoisomers of a compound of formula (I) or of different compounds of formula (I) or a composition obtainable by the below method of the invention and at least one solvent.

In the context of the present invention, a "solvent" serves for the dilution of the compound of formula (I), or a stereoisomer thereof, or a mixture of different compounds of formula (I), or a mixture of stereoisomers of a compound of formula (I) or of different compounds of formula (I) or a composition obtainable by the below method of the invention to be used according to the invention without having its own odiferous properties. Some solvents have fixing properties at the same time.

The one or more solvent(s) can be present in the composition from 0.01 to 99% by weight based on the composition. In a preferred embodiment of the invention, the composition comprise 0.1 to 90 weight %, preferably 0.5 to 80 weight % of solvent(s) based on the composition. The amount of solvent(s) can be chosen depending on the composition. In one embodiment of the invention, the composition comprises 0.05 to 10 weight %, preferably 0.1 to 5 weight %, more preferably 0.2 to 3 weight % based on the composition. In one embodiment of the invention, the composition comprises 20 to 70 weight %, preferably 25 to 50 weight % of solvent(s) based on the composition.

Preferred solvents are ethanol, dipropylene glycol (DPG), propylene glycol, 1,2-butylene glycol, glycerol, diethylene glycol monoethyl ether, diethyl phthalate (DEP), isopropyl myristate (IPM), triethyl citrate (TEC), and benzyl benzoate (BB). Especially preferred solvents are selected from the group consisting of ethanol, propylene glycol, dipropylene glycol, triethyl citrate, benzyl benzoate and isopropyl myristate.

In a preferred embodiment of the invention, the solvent is selected from the group consisting of ethanol, isopropanol, diethylene glycol monoethyl ether, glycerol, propylene glycol, 1,2-butylene glycol, dipropylene glycol, triethyl citrate and isopropyl myristate.

According to a further aspect, the compounds of formula (I), the stereoisomers thereof, the mixtures of different compounds of formula (I), the mixtures of stereoisomers of a compound of formula (I) or of different compounds of formula (I) and the composition obtainable by the below method of the invention are suitable for use in surfactant-containing compositions. According to their characteristic scent profiles, they can especially be used for the perfuming of surfactant-containing compositions such as, for example, cleaners (in particular laundry care products and all-purpose cleaners).

One embodiment of the invention is therefore directed to a composition comprising a compound of formula (I), or a stereoisomer thereof, or a mixture of different compounds of formula (I), or a mixture of stereoisomers of a compound of formula (I) or of different compounds of formula (I) or a composition obtainable by the below method of the invention and at least one surfactant.

The surfactant(s) may be selected from anionic, nonionic, cationic and/or amphoteric or zwitterionic surfactants. Surfactant-containing compositions, such as for example shower gels, foam baths, shampoos, etc., preferably contain at least one anionic surfactant.

The compositions according to the invention usually contain the surfactant(s), in the aggregate, in a quantity of 0 to 40% by weight, preferably 0 to 20% by weight, more preferably 0.1 to 15% by weight, and particularly 0.1 to 10% by weight, based on the total weight of the composition. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)

yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Zwitterionic surfactants are surface-active compounds which contain at least one quaternary ammonium group and at least one —COO⁻ or —SO₃⁻ group in the molecule. Particularly suitable zwitterionic surfactants are the so-called betaines, such as the N-alkyl-N,N-dimethyl ammonium glycinates, for example, cocoalkyl dimethyl ammonium glycinate, N-acylaminopropyl-N,N-dimethyl ammonium glycinates, for example, cocoacylaminopropyl dimethyl ammonium glycinate, and 2-alkyl-3-carboxymethyl-3-hydroxyethyl imidazolines, containing 8 to 18 carbon atoms in the alkyl or acyl group, and cocoacylaminoethyl hydroxyethyl carboxymethyl glycinate. The fatty acid amide derivative known under the CTFA name of Cocamidopropyl Betaine is particularly preferred.

Ampholytic surfactants are also suitable, particularly as co-surfactants. Ampholytic surfactants are surface-active compounds which, in addition to a $C_8$-$C_{18}$ alkyl or acyl group, contain at least one free amino group and at least one —COOH or —SO₃H group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalk-ylaminopropionate, cocoacylaminoethyl aminopropionate and acyl sarcosine.

Anionic surfactants are characterized by a water-solubilizing anionic group such as, for example, a carboxylate, sulfate, sulfonate or phosphate group and a lipophilic group.

Dermatologically safe anionic surfactants are known to the practitioner in large numbers from relevant textbooks and are commercially available. They are, in particular, alkyl sulfates in the form of their alkali metal, ammonium or alkanolammonium salts, alkylether sulfates, alkylether carboxylates, acyl isethionates, acyl sarcosinates, acyl taurines containing linear $C_{12}$-$C_{18}$ alkyl or acyl groups and sulfosuccinates and acyl glutamates in the form of their alkali metal or ammonium salts.

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example, cetyl trimethyl ammonium chloride, stearyl trim ethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as, for example, the dialkyl ammonium methosulfates and methyl hydroxyalkyl dialkoyloxyalkyl ammonium methosulfates marketed under the name of Stepantexe and the corresponding products of the Dehyquart® series, may be used as cationic surfactants. "Esterquats" are generally understood to be quaternized fatty acid triethanolamine ester salts. They can provide the compositions with particular softness. They are known substances which are prepared by the relevant methods of organic chemistry. Other cationic surfactants suitable for use in accordance with the invention are the quaternized protein hydrolyzates.

One embodiment of the invention is directed to a composition comprising a compound of formula (I), or a stereoisomer thereof, or a mixture of different compounds of formula (I), or a mixture of stereoisomers of a compound of formula (I) or of different compounds of formula (I) or a composition obtainable by the below method of the invention and at least one oil component.

The oil components are typically present in a total quantity of 0.1 to 80, preferably 0.5 to 70, more preferably 1 to 60, even more preferably 1 to 50% by weight, in particular 1 to 40% by weight, more particularly 5 to 25% by weight and specifically 5 to 15% by weight based on the composition.

The oil components may be selected, for example, from Guerbet alcohols based on fatty alcohols containing 6 to 18 and preferably 8 to 10 carbon atoms and other additional esters, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl ole-ate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18}$-$C_{38}$-alkyl-hydroxycarboxylic acids with linear or branched $C_6$-$C_{22}$-fatty alcohols, more especially dioctyl malate, esters of linear and/or branched fatty acids with polyhydric alcohols (for example propylene glycol, dimer diol or trimer triol), triglycerides based on $C_6$-$C_{10}$-fatty acids, liquid mono-, di- and triglyceride mixtures based on $C_6$-$C_{18}$-fatty acids, esters of $C_6$-$C_{22}$-fatty alcohols and/or Guerbet alcohols with aromatic carboxylic acids, more particularly benzoic acid, esters of dicarboxylic acids with polyols containing 2 to 10 carbon atoms and 2 to 6 hydroxyl groups, vegetable oils, branched primary alcohols, substituted cyclohexanes, linear and branched $C_6$-$C_{22}$-fatty alcohol carbonates such as, for example, dicaprylyl carbonate (Cetiol® CC), Guerbet carbonates based on fatty alcohols containing 6 to 18 and preferably 8 to 10 carbon atoms, esters of benzoic acid with linear and/or branched $C_6$ to $C_{22}$-alcohols (for example Finsolv® TN), linear or branched, symmetrical or nonsymmetrical dialkyl ethers containing 6 to 22 carbon atoms per alkyl group such as, for example, dicaprylyl ether (Cetiol® OE), ring opening products of epoxidized fatty acid esters with polyols and hydrocarbons or mixtures thereof.

The compounds of formula (I), the stereoisomers thereof, the mixtures of different compounds of formula (I), the mixtures of stereoisomers of a compound of formula (I) or of different compounds of formula (I) and the composition obtainable by the below method of the invention can be used in a wide range of aroma chemical compositions.

The olfactory properties, the substance properties (such as solubility in customary solvents and compatibility with further customary constituents of such compositions), as well as the toxicological acceptability of the compound of formula (I) underline its particular suitability for the stated use purposes and compositions.

Suitable aroma chemical compositions are for example perfume compositions, body care compositions, hygiene articles, cleaning compositions, textile detergent compositions, compositions for scent dispensers, foods, food supplements, pharmaceutical compositions and crop protection compositions.

Perfume compositions can be selected from fine fragrances, air fresheners in liquid form, gel-like form or a form applied to a solid carrier, aerosol sprays, scented cleaners, perfume candles and oils, such as lamp oils or oils for massage.

Examples for fine fragrances are perfume extracts, Eau de Parfums, Eau de Toilettes, Eau de Colognes, Eau de Solide and Extrait Parfum.

Body care compositions include cosmetic compositions and products for oral and dental hygiene, and can be selected from after-shaves, pre-shave products, splash colognes, solid and liquid soaps, shower gels, shampoos, shaving soaps, shaving foams, bath oils, cosmetic emulsions of the oil-in-water type, of the water-in-oil type and of the water-in-oil-in-water type, such as e.g. skin creams and lotions, face creams and lotions, sunscreen creams and lotions, after-sun creams and lotions, hand creams and lotions, foot creams and lotions, hair removal creams and lotions, after-shave creams and lotions, tanning creams and lotions, hair care products such as e.g. hairsprays, hair gels, setting hair lotions, hair conditioners, hair shampoo, permanent and semi-permanent hair colorants, hair shaping compositions such as cold waves and hair smoothing compositions, hair tonics, hair creams and hair lotions, deodorants and antiperspirants such as e.g. underarm sprays, roll-ons, deodorant sticks and deodorant creams, products of decorative cosmetics such as e.g. eye-liners, eye-shadows, nail varnishes, make-ups, lipsticks and mascara, and products for oral and dental hygiene, such as toothpaste, dental floss, mouth wash, breath fresheners, dental foam, dental gels and dental strips.

Hygiene articles can be selected from joss sticks, insecticides, repellents, propellants, rust removers, perfumed freshening wipes, armpit pads, baby diapers, sanitary towels, toilet paper, cosmetic wipes, pocket tissues, dishwasher and deodorizer.

Cleaning compositions, such as e.g. cleaners for solid surfaces, can be selected from perfumed acidic, alkaline and neutral cleaners, such as e.g. floor cleaners, window cleaners, dishwashing detergents both for handwashing and machine washing use, bath and sanitary cleaners, scouring milk, solid and liquid toilet cleaners, powder and foam carpet cleaners, waxes and polishes such as furniture polishes, floor waxes, shoe creams, disinfectants, surface disinfectants and sanitary cleaners, brake cleaners, pipe cleaners, limescale removers, grill and oven cleaners, algae and moss removers, mold removers, facade cleaners.

Textile detergent compositions can be selected from liquid detergents, powder detergents, laundry pretreatments such as bleaches, soaking agents and stain removers, fabric softeners, washing soaps, washing tablets.

Food means a raw, cooked, or processed edible substance, ice, beverage or ingredient used or intended for use in whole or in part for human consumption, or chewing gum, gummies, jellies, and confectionaries.

A food supplement is a product intended for ingestion that contains a dietary ingredient intended to add further nutritional value to the diet. A dietary ingredient may be one, or any combination, of the following substances: a vitamin, a mineral, an herb or other botanical, an amino acid, a dietary substance for use by people to supplement the diet by increasing the total dietary intake, a concentrate, metabolite, constituent, or extract.

Food supplements may be found in many forms such as tablets, capsules, softgels, gelcaps, liquids, or powders.

Pharmaceutical compositions comprise compositions which are intended for use in the diagnosis, cure, mitigation, treatment, or prevention of disease as well as articles (other than food) intended to affect the structure or any function of the body of man or other animals.

Crop protection compositions comprise compositions which are intended for the managing of plant diseases, weeds and other pests (both vertebrate and invertebrate) that damage agricultural crops and forestry.

The compositions according to the invention can further comprise one or more substances, such as, for example: preservatives, abrasives, anti-acne agents, agents to combat skin aging, antibacterial agents, anti-cellulite agents, anti-dandruff agents, anti-inflammatory agents, irritation-preventing agents, irritation-alleviating agents, antimicrobial agents, antioxidants, astringents, sweat-inhibiting agents, antiseptics, antistatics, binders, buffers, carrier materials, chelating agents, cell stimulants, cleaning agents, care agents, hair removal agents, surface-active substances, deodorizing agents, antiperspirants, emulsifiers, enzymes, essential oils, fibers, film formers, fixatives, foam formers, foam stabilizers, substances for preventing foaming, foam boosters, fungicides, gelling agents, gel-forming agents, hair care agents, hair shaping agents, hair smoothing agents, moisture-donating agents, moisturizing substances, humectant substances, bleaching agents, strengthening agents, stain removal agents, optical brighteners, impregnating agents, soil repellents, friction-reducing agents, lubricants, moisturizing creams, ointments, opacifiers, plasticizers, covering agents, polish, shine agents, polymers, powders, proteins, refatting agents, exfoliating agents, silicones, skin-calming agents, skin-cleansing agents, skin care agents, skin-healing agents, skin lightening agents, skin-protective agents, skin-softening agents, cooling agents, skin-cooling agents, warming agents, skin-warming agents, stabilizers, UV-absorbent agents, UV filters, fabric softeners, suspending agents, skin-tanning agents, thickeners, vitamins, oils, waxes, fats, phospholipids, saturated fatty acids, mono- or polyunsaturated fatty acids, a-hydroxy acids, polyhydroxy fatty acids, liquefiers, dyes, color-protection agents, pigments, anticorrosives, polyols, surfactants, electrolytes, organic solvents or silicone derivatives.

The compounds of formula (I), the stereoisomers thereof, the mixtures of different compounds of formula (I), the mixtures of stereoisomers of a compound of formula (I) or of different compounds of formula (I) and the composition obtainable by the below method, as well as the aroma chemical compositions according to the invention comprising them can also be in microencapsulated form, spray-dried form, in the form of inclusion complexes or in the form of extrusion products. The properties can be further optimized by so-called "coating" with suitable materials with regard to a more targeted release of the scent, for which purpose preferably waxy synthetic substances such as e.g. polyvinyl alcohol are used.

The microencapsulation can take place for example by the so-called coacervation method with the help of capsule materials, e.g. made of polyurethane-like substances or soft gelatin. The spray-dried perfume oils can be produced for example by spray-drying an emulsion or dispersion comprising a compound of formula (I), or a stereoisomer thereof, or a mixture of different compounds of formula (I), or a mixture of stereoisomers of a compound of formula (I) or of different compounds of formula (I) or a composition obtainable by the below method of the invention, wherein carrier substances that can be used are modified starches, proteins, dextrin and vegetable gums. Inclusion complexes can be prepared e.g. by introducing dispersions of fragrance compositions and cyclodextrins or urea derivatives into a suitable solvent, e.g. water. Extrusion products can be produced by melting a compound of formula (I), or a stereoisomer thereof, or a mixture of different compounds of formula (I), or a mixture of stereoisomers of a compound of formula (I) or of different compounds of formula (I) or a composition obtainable by the below method of the invention with a suitable wax-like substance and by extrusion with subsequent solidification, optionally in a suitable solvent, e.g. isopropanol.

Generally, the total amount of the compounds of formula (I), the stereoisomers thereof, the mixtures of different compounds of formula (I), the mixtures of stereoisomers of a compound of formula (I) or of different compounds of formula (I) or the composition obtainable by the below method of the invention in the aroma chemical compositions according to the present invention is typically adapted to the particular intended use or the intended application and can, thus, vary over a wide range. As a rule, the customary standard commercial amounts for scents are used.

The compositions according to the invention can comprise the compounds of formula (I) or the stereoisomers thereof in an overall amount of from 0.001 to 99.9% by weight, preferably from 0.01 to 90% by weight, more preferably from 0.05 to 80%, in particular from 0.1 to 60% by weight, more particularly from 0.1 to 40% by weight, e.g. from 0.1 to 10% by weight or 0.1 to 15% by weight, based on the total weight of the composition.

In one embodiment of the invention, the compositions comprise the compounds of formula (I) or the stereoisomers thereof in an overall amount of from 0.001 to 5 weight %, preferably from 0.01 to 2 weight % based on the total weight of the composition.

A further embodiment of the invention is directed to a method of preparing a perfume composition, body care composition, hygiene article, cleaning composition, textile detergent composition, composition for scent dispensers, food, food supplement, pharmaceutical composition or crop protection composition, comprising including a compound of formula (I), or a stereoisomer thereof, or a mixture of different compounds of formula (I), or a mixture of stereoisomers of a compound of formula (I) or of different compounds of formula (I) or a composition obtainable by the below method of the invention in a perfume composition, body care composition, hygiene article, cleaning composition, textile detergent composition, composition for scent dispensers, food, food supplement, pharmaceutical composition or crop protection composition.

In one embodiment the invention is directed to a method for imparting a minty, fresh, green, herbal, woody, dried fruits note to a perfume composition, body care composition, hygiene article, cleaning composition, textile detergent composition, composition for scent dispensers, food, food supplement, pharmaceutical composition or crop protection composition, which comprises including the compound of formula (IA) or one or more stereoisomers thereof in a perfume composition, body care composition, hygiene article, cleaning composition, textile detergent composition, composition for scent dispensers, food, food supplement, pharmaceutical composition or crop protection composition.

Another embodiment the invention is directed to a method for imparting a herbal, woody, dried fruits, fatty note to a perfume composition, body care composition, hygiene article, cleaning composition, textile detergent composition, composition for scent dispensers, food, food supplement, pharmaceutical composition or crop protection composition, which comprises including the compound of formula (IB) or a stereoisomer thereof or a mixture of different stereoisomers thereof in a perfume composition, body care composition, hygiene article, cleaning composition, textile detergent composition, composition for scent dispensers, food, food supplement, pharmaceutical composition or crop protection composition.

Yet another embodiment the invention is directed to a method for imparting a herbal, woody, dried fruits, fatty note to a perfume composition, body care composition, hygiene article, cleaning composition, textile detergent composition, composition for scent dispensers, food, food supplement, pharmaceutical composition or crop protection composition, which comprises including a mixture of the compounds of formula (IB) and (IE), in particular a 3:1 mixture of the compounds of formula (IB) and (IE), or a stereoisomer thereof or a mixture of different stereoisomers thereof in a perfume composition, body care composition, hygiene article, cleaning composition, textile detergent composition, composition for scent dispensers, food, food supplement, pharmaceutical composition or crop protection composition.

The compounds of formula (I), mixtures of different compounds (I) as well as single stereoisomers or mixtures of stereoisomers thereof can be prepared by methods principally known in the art.

For instance, compounds (IA) can be prepared by hydrogenation of the corresponding pyran or dihydropyran precursors (i.e. of 3,5-diethyl-2-propyl-pyrans, such as 3,5-diethyl-2-propyl-2H-pyran, 3,5-diethyl-2-propyl-4H-pyran or 3,5-diethyl-2-propyl-6H-pyran; or 3,5-diethyl-2-propyl-dihydropyrans, such as 3,5-diethyl-2-propyl-3,4-dihydro-2H-pyran, 3,5-diethyl-2-propyl-4,6-dihydro-5H-pyran, 3,5-diethyl-2-propyl-3,6-dihydro-2H-pyran or 3,5-diethyl-2-propyl-5,6-dihydro-2H-pyran, i.e. by hydrogenation of any one of the compounds (IB) to (IH); and specifically of 3,5-diethyl-2-propyl-4,6-dihydro-5H-pyran and/or 3,5-diethyl-2-propyl-3,4-dihydro-2H-pyran). Suitable hydrogenation conditions are described below. The hydrogenation product can then be subjected to suitable separation methods if the compound (IA) is to be separated into its different stereoisomers.

3,5-Diethyl-2-propyl-pyrans and 3,5-diethyl-2-propyl-dihydropyrans are in turn for example available by following reactions: n-Butanal is subjected to an aldol reaction under conditions which avoid the formation of the condensation product, i.e. the elimination of water from the butyraldol (2-ethyl-3-hydroxyhexanal). Such conditions are known to the skilled person and described, for example, in Organikum, $22^{nd}$ edition, 2004; Wiley-VCH. The reaction is carried out under basic conditions, using, e.g. aqueous or methanolic alkali metal hydroxides as catalysts, e.g. aqueous or methanolic sodium or potassium hydroxide. Importantly, the reaction temperature has to be rather low, in particular at most 35° C., preferably at most 30° C., e.g. from 5 to 25° C. After neutralization of the reaction mixture and if desired isolation of the reaction product 2-ethyl-3-hydroxyhexanal, the hydroxy group of this compound is expediently protected. Suitable protective groups are for example described in T. Greene and P. Wuts, Protective Groups in Organic Synthesis ($3^{rd}$ ed.), John Wiley & Sons, NY (1999). Suitable are silyl protective groups, such as trimethylsilyl (TMS), triethylsilyl (TES), triisopropylsilyl (TIPS), tert-butyldimethylsilyl (TBDMS) or tert-butyldiphenylsilyl (TBDPS). Alternatively, the reaction mixture can be quenched with the chloride of the protective group to give directly the protected compound. The protected compound can then be reacted in an aldol condensation with another molecule of n-butanal, this time under such conditions that aldol condensation takes place, i.e. at elevated temperatures of at least 40° C. Subsequent deprotection of the aldol condensation product yields 2,4-diethyl-5-hydroxyoct-2-en-al. This is then subjected to a ring-closing reaction in which the oxygen atom of the hydroxy group nucleophilically attacks the carbonyl group. Elimination of water eventually yields 3,5-diethyl-2-propyl-pyran.

Expediently, however, the compounds of formula (I) as well as single stereoisomers or mixtures of stereoisomers thereof are available as by-products in the production of 2-ethylhexanal from 2-ethylhexenal or of 2-ethylhexanol from 2-ethylhexenal.

2-Ethylhexenal is in turn generally produced in an aldol condensation of 2 molecules of n-butyraldehyde; and it is assumed that the compounds of formula (I) or stereoisomers thereof are formed as by-products during said aldol reaction. To be more precise, it is assumed that a minor part of the primary aldol product 2-ethyl-3-hydroxy-hexanal, instead of eliminating water, reacts with a further n-butyraldehyde molecule in an aldol condensation step, and the resulting 2,4-diethyl-5-hydroxyoctenal, under the reaction conditions of the conversion of 2-ethylhexenal to 2-ethylhexanal, can give a 6-membered oxygen-containing ring with 3,5-diethyl-2-propyl substitution.

Accordingly, in a further aspect, the invention relates to a method for preparing the compound of formula (I) or a stereoisomer thereof or a mixture of stereoisomers thereof as defined above, comprising
(i) subjecting n-butanal to an aldol condensation reaction;
(ii) subjecting the reaction product of step (i) containing 2-ethylhexenal to catalytic hydrogenation in the presence of a palladium, platinum or ruthenium catalyst;
(iii) removing 2-ethylhexanal formed in step (ii) by distillation;
(iv.1) subjecting the bottom fraction of the distillation in step (iii) to a distillation; and
(v.1.1) isolating from the distillation product of step (iv.1) [i.e. from the head product of the distillation in step (iv.1)] a compound of formula (I) in which
  $R^1$ and $R^2$, together with the carbon atoms to which they are bound, form a C—C double bond and $R^3$, $R^4$ and $R^5$ are hydrogen [i.e. compound (IB)]; or
  $R^2$ and $R^3$, together with the carbon atoms to which they are bound, form a C—C double bond and $R^1$, $R^4$ and $R^5$ are hydrogen [i.e. compound (IC)]; or
  $R^3$ and $R^4$, together with the carbon atoms to which they are bound, form a C—C double bond and $R^1$, $R^2$ and $R^5$ are hydrogen [i.e. compound (ID)]; or
  $R^4$ and $R^5$, together with the carbon atoms to which they are bound, form a C—C double bond and $R^1$, $R^2$ and $R^3$ are hydrogen [i.e. compound (IE)]; or
  $R^1$ and $R^2$, together with the carbon atoms to which they are bound, form a C—C double bond, $R^3$ and $R^4$, together with the carbon atoms to which they are bound, form a C—C double bond, and $R^5$ is hydrogen [i.e. compound (IF)]; or
  $R^1$ and $R^2$, together with the carbon atoms to which they are bound, form a C—C double bond, $R^4$ and $R^5$, together with the carbon atoms to which they are bound, form a C—C double bond, and $R^3$ is hydrogen [i.e. compound (IG)]; or
  $R^2$ and $R^3$, together with the carbon atoms to which they are bound, form a C—C double bond, $R^4$ and $R^5$, together with the carbon atoms to which they are bound, form a C—C double bond, and $R^1$ is hydrogen [i.e. compound (IH)]; or
  a mixture containing at least two of these compounds; or
  a mixture containing at least one of this compounds and a compound (I) in which
  $R^1$, $R^2$, $R^3$, $R^4$ and $R^5$ are hydrogen [i.e. compound (IA)]; or one or more stereoisomers of the above compounds;
or
(v.1.2) subjecting the distillation product of step (iv.1) [i.e. the head product of the distillation in step (iv.1)] to catalytic hydrogenation; and
(vi.1) isolating the compound of formula (I) in which $R^1$, $R^2$, $R^3$, $R^4$ and $R^5$ are hydrogen [i.e. compound (IA)] or one or more stereoisomers thereof or a mixture containing the compound of formula (I) in which $R^1$, $R^2$, $R^3$, $R^4$ and $R^5$ are hydrogen [i.e. compound (IA)] or one or more stereoisomers thereof;
or
(iv.2) subjecting the bottom fraction of the distillation in step (iii) to catalytic hydrogenation; and
(v.2) isolating the compound of formula (I) in which $R^1$, $R^2$, $R^3$, $R^4$ and $R^5$ are hydrogen [i.e. compound (IA)] or one or more stereoisomers thereof or a mixture containing the compound of formula (I) in which $R^1$, $R^2$, $R^3$, $R^4$ and $R^5$ are hydrogen [i.e. compound (IA)] or one or more stereoisomers thereof.

This method is termed in the following method A.

In the aldol condensation step (i) first the butyraldol is formed, which eliminates water to give 2-ethylhexenal. The aldol condensation is carried out under customary conditions for aldol condensations, preferably under basic conditions, using, for example, a 0.5 to 5% by weight, preferably 0.8 to 5% by weight, more preferably 0.8 to 4% by weight, in particular 1 to 4% by weight, specifically 1 to 3% by weight, aqueous solution of an alkali metal hydroxide, in particular sodium or potassium hydroxide, specifically sodium hydroxide, as a catalyst. The weight percentages relate to the weight of the solution. Since the alkali metal hydroxide acts as a catalyst, it may be used in very low amounts. Typically, however, the alkali metal hydroxide solution is used in such an amount that the molar ratio of n-butanal and the alkali metal hydroxide is in the range of from 100:1 to 10:1, in particular from 60:1 to 15:1 and specifically from 30:1 to 20:1. n-Butanal and the alkali metal hydroxide solution have to be mixed thoroughly, using e.g. a stirring vessel or a mixing pump. The reaction is generally carried out at an elevated temperature of at least 40° C., such as from 40 to 170° C.; e.g. of at least 50° C., such as from 50 to 170° C.; and is preferably carried out at a temperature of from 70 to 170° C., more preferably 80 to 160° C., and in particular from 80 to 150° C., e.g. from 80 to 100° C. or from 100 to 120° C. or from 130 to 150° C.; and specifically from 80 to 100° C. Depending on the temperature, the reaction pressure is preferably from 0.1 to 0.7 MPa. In industrial scale reactions, the reaction time is generally from 0.2 to 5 minutes, preferably from 0.5 to 4 minutes, in particular from 1 to 3 minutes, but can also be longer, such as up to 2 hours or up to 1 hour; especially if on a smaller scale.

After completion of the reaction, the mixture is generally cooled, whereupon two phases form, which are separated. The aqueous phase containing the reaction water and the alkali hydroxide can generally be recirculated to the aldol reaction step. The organic phase containing crude 2-ethylhexenal is used in step (ii), generally without further purification.

In step (ii), the reaction product of step (i) containing 2-ethylhexenal is subjected to a catalytic hydrogenation in the presence of a palladium, platinum or ruthenium catalyst, in particular of a palladium catalyst. Suitable hydrogenation conditions and methods are known in the art and described, for example, in U.S. Pat. No. 5,756,856 and the references cited therein; and in particular in DE 2008128. The hydrogenation conditions are such that 2-ethylhexenal is reacted to 2-ethylhexenal; i.e. such that the carbonyl group remains intact.

The palladium, platinum or ruthenium catalyst is generally supported, e.g. on $Al_2O_3$, $SiO_2$, in particular amorphous silicon dioxide, barium carbonate, calcium carbonate, magnesium carbonate or carbon, e.g. activated carbon or carbon black. Preference is given to $Al_2O_3$. The catalyst is preferably used in the presence of an alkali metal-, earth alkaline metal-, aluminum-, zinc-, iron-, chromium- and/or lanthanide-containing compound, e.g. an oxide thereof. Preference is given to alkali metal-, earth alkaline metal-, iron- or lanthanide-containing compounds, especially to oxides thereof. Specifically an alkali metal- or iron-containing compound or a mixture thereof is used, especially an alkali metal oxide, an iron oxide or a mixture thereof. The overall weight ratio of palladium, platinum or ruthenium to such a compound is generally in the range of from 1:100 to 100:1, preferably 1:100 to 2:1, more preferably from 1:100 to 1:1 and in particular from 1:20 to 1:1.5. The reaction temperature is generally from 50 to 200° C., preferably from 60 to 150° C., more preferably from 60 to 120° C., in particular from 70 to 100° C. and specifically from 75 to 85° C. The hydrogen pressure is generally from 2 to 100 bar absolute (0.2 to 10 MPa), preferably from 5 to 50 bar absolute (0.5 to 5 MPa), in particular from 10 to 30 bar absolute (1 to 3 MPa) and specifically from 15 to 30 bar absolute (1.5 to 3.0 MPa). The hydrogenation can be carried out in a variety of reactors known for this purpose, such as a serial loop reactor as described in U.S. Pat. No. 5,756,856, but also in simpler reactors, as described for example in DE 2008128. Preference is given to fixed bed reactors, in particular to trickle bed reactors.

The reaction product of the hydrogenation of step (ii) containing the hydrogenation product 2-ethylhexanal is then, generally without further purification after separation of the reaction product from the catalyst, subjected to a distillation step (iii) in which 2-ethylhexanal is removed. The distillation is generally carried out at atmospheric or reduced pressure, e.g. at from 100 mbar (0.01 MPa) to atmospheric pressure, preferably from 200 to 1000 mbar (0.02 to 0.1 MPa), in particular from 500 to 900 mbar (0.05 to 0.09 MPa), and the external temperature is generally about 10 to 50° C. higher than the boiling point of 2-ethylhexanal at the given pressure, e.g. from 100 to 210° C. The distillation can be carried out in one rectification column or in a series of columns to which the sump or bottom fraction of the previous column is fed.

After all or virtually all 2-ethylhexanal has been distilled of, the bottom fraction (also called sump) of the distillation in step (iii) is subjected to a distillation step (iv.1) to separate the lower boiling components of the sump obtained after the distillation in step (iii) from the high-boiling components. This distillation step (iv.1) is typically carried out at reduced pressure and in particular at a lower pressure than step (iii), e.g. at from 1 to 50 mbar (100 Pa to 5 kPa), preferably at from 1 to 30 mbar (100 Pa to 3 kPa), e.g. at from 5 to 15 mbar (500 Pa to 1500 Pa). The values refer to the head pressure of the distillation apparatus. The temperature depends on the applied vacuum and is generally in the range given above in step (iii). The head temperature is generally in the range of 80 to 120° C., specifically at 90 to 100° C. at 5 to 15 mbar head pressure. Generally it is not necessary to carry out the distillation as a rectification, so that simpler distillation apparatuses can be used, provided that vacuum in the required range can be applied. Examples are falling film evaporators or thin film evaporators.

After step (iv.1), either one or more of the compounds listed in step (v.1.1) (which are the compounds (IB) to (IH) or a mixture or one or more of these compounds with compound (IA) or one or more stereoisomers of said compounds are isolated from the head product of distillation step (iv.1) [step (v.1.1)] or, alternatively, the head product of distillation step (iv.1) is submitted to a catalytic hydrogenation [step (v.1.2)].

Isolation in step (v.1.1) can be carried out by usual means of the art, such as distillative, extractive or chromatographic methods.

For instance, the head product of distillation step (iv.1) is subjected to a fractional distillation and one or more fractions containing one or more of the compounds IB to IH or stereoisomers thereof or mixtures of stereoisomers thereof are isolated. Preferably, the fractionation is carried out at reduced pressure, e.g. at 0.1 to 500 mbar, preferably at 0.1 to 100 mbar, in particular at 1 to 50 mbar and specifically at 1 to 15 mbar, the values denoting the pressure at the head of a rectification column. Fractions containing the compound (s) IB to IH or stereoisomers thereof or mixtures of stereoisomers thereof can be identified by usual means, such as GC/MS and/or NMR. Usually they have a boiling point of ca. 95° C. at 5 to 15 mbar.

If desired, the one or more fractions containing the compound(s) IB to IH or stereoisomers thereof or mixtures of stereoisomers thereof can be resubmitted to one or more further purification methods, e.g. to one or more (further) fractional distillations or chromatographic methods, such as classical column chromatography, flash chromatography, MPLC or preparative HPLC, in order to further enrich or purify them.

Other suitable methods for isolating said compounds are the chromatographic separation of the products contained in the head product of distillation step (iv.1), such as column chromatography, flash chromatography, MPLC or preparative HPLC. In a specific embodiment, the isolation step (v.1.1) applies chromatographic methods.

The method of the invention comprising step (v.1.1) is preferably used for providing compound (IB) and/or (IE) or one or more stereoisomers thereof, optionally in admixture with compound (IA) or one or more stereoisomers thereof. More preferably, the method of the invention comprising step (v.1.1) is used for providing compound (IB) or one or more stereoisomers thereof; optionally in admixture with compound (IA) or one or more stereoisomers thereof; or for providing a mixture containing compounds (IB) and (IE) or one or more stereoisomers thereof and optionally also compound (IA) or one or more stereoisomers thereof. If compound (IA) is contained, this is preferably present in an amount of at most 30% by weight, more preferably at most 20% by weight, in particular at most 10% by weight, more particularly at most 5% by weight, specifically at most 2% by weight, more specifically at most 1% by weight, based on the overall weight of compounds (IA), (IB) and (IE) (if present).

The hydrogenation step (v.1.2) is typically carried out in liquid phase with hydrogen in the presence of a hydrogenation catalyst, but can also be carried out in gas phase. Preferably, the hydrogenation step is carried out in liquid phase.

Suitable hydrogenation catalysts for step (v.1.2) are those customarily used in the hydrogenation of olefinic carbon-carbon double bonds. The catalysts may be used either in heterogeneous phase or as homogeneous catalysts. The hydrogenation catalysts preferably comprise at least one metal of group VIII and also VIIa (group VIIA according to the former IUPAC recommendation=group 7 according to the IUPAC recommendation of 1985).

Suitable metals of group VIII are selected from the group consisting of ruthenium, cobalt, rhodium, nickel, palladium and platinum. A suitable metal of group VIIa is rhenium. The metals may also be used in the form of mixtures. Metals of group VIII may also comprise small amounts of further metals, for example metals of group VIIa, in particular rhenium, or metals of group Ib (=group 11 according to the IUPAC recommendation of 1985), i.e. copper, silver or gold. Particularly suitable metals of group VIII are ruthenium, nickel, palladium and platinum. The catalyst especially comprises palladium as the catalytically active species, or comprises copper and nickel.

When a heterogeneous catalyst is used, it is suitably present in finely divided form. The finely divided form is achieved, for example, as follows:

a) Black catalyst: shortly before use as a catalyst, the metal is deposited reductively from the solution of one of its salts.

b) Adams catalyst: the metal oxides, in particular the oxides of platinum and palladium, are reduced in situ by the hydrogen used for the hydrogenation.

c) Skeletal or Raney catalyst: the catalyst is prepared as a "metal sponge" from a binary alloy of the metal (in particular nickel or cobalt) with aluminum or silicon by leaching out one partner with acid or alkali. Residues of the original alloy partner often act synergistically.

d) Supported catalyst: black catalysts can also be precipitated on the surface of a support substance. Suitable supports and support materials are described below.

The heterogeneous catalyst can be in the form of a fine powder, of granules, molded bodies, extrudates, aerogels, monoliths or in form of nets (for example honeycombs). In contrast to powder and granules, molded bodies have a defined particle size typically of some mm, e.g. 1, 2, 3, 5, 6 or 10 mm. The size relates to the distance between those two points on the surface of the body which are furthest apart from each other. Typical forms are pills, beads, spheres, cylinders, trilobes and the like. Molded bodies and monoliths are generally forms of supported catalysts. Powder and granules can be forms of both supported and unsupported catalysts. Nets are generally unsupported catalyst forms, but can also be supported forms.

The supports may be any variety of materials on which catalytically active material can be coated. Typically, the support material has a high surface area and is stable under the applied reaction conditions. It may consist of metallic or nonmetallic, porous or nonporous material. Suitable metallic materials are, for example, highly alloyed stainless steels. Suitable nonmetallic materials are, for example, mineral materials, for example natural and synthetic minerals, glasses or ceramics, carbon, for example activated carbon or carbon black, plastics, for example synthetic or natural polymers, or a combination thereof. Preferred support materials are carbon, in particular activated carbon, silicon dioxide, in particular amorphous silicon dioxide, alumina, titanium oxide, chromium oxide, zirconium oxide, zinc oxide, and also the sulfates and carbonates of the alkaline earth metals, calcium carbonate, calcium sulfate, magnesium carbonate or magnesium sulfate. As already explained above, the supported heterogeneous catalysts may be used in the form of powders, granules, molded bodies, such as pills, beads, spheres, cylinders, trilobes and the like, extrudates, monoliths, packed beds, aerogels, or any other manufactured configuration.

The catalyst may be applied to the support by customary processes, for example by impregnating, wetting or spraying the support with a solution which comprises the catalyst or a suitable precursor thereof.

The hydrogenation step using a heterogeneous catalyst can be carried out in suspension or using a fixed bed.

It is also possible to use homogeneous hydrogenation catalysts, such as, for example, the Wilkinson catalyst and derivatives thereof, or BINAP-ruthenium complexes, e.g. $Ru(OAc)_2$-(S)-BINAP. However, disadvantages of use of homogeneous catalysts are their preparation costs. Therefore, preference is given to using heterogeneous hydrogenation catalysts.

The catalytic metal is in particular used in supported form or as metal sponge. Examples of supported catalysts are palladium, nickel, copper, mixtures of nickel and copper, or ruthenium on carbon, in particular activated carbon, silicon dioxide, in particular on amorphous silicon dioxide, calcium carbonate, magnesium carbonate or alumina. A suitable metal sponge is for example Raney nickel.

The metallic catalysts may also be used in the form of their oxides, in particular palladium oxide, platinum oxide, copper oxide or nickel oxide, which are then reduced under the hydrogenation conditions to the corresponding metals.

Metals applied in the form of their salts have generally to be activated before use, typically by reduction to the elemental form. In many cases, they are activated in situ under the hydrogenation conditions. Alternatively, a separate activation step precedes the hydrogenation step.

In a particular embodiment, palladium on carbon is used.

In another particular embodiment, Cu/Ni on silica is used. This may contain minor amounts of further transition metals, in particular of group 7 metals, such as Mn.

The reaction temperature is generally from 50 to 250° C., preferably from 80 to 220° C., in particular from 100 to 200° C. and specifically from 120 to 200° C. The hydrogen pressure is generally from 2 to 300 bar absolute (0.2 to 30 MPa), preferably from 5 to 250 bar absolute (0.5 to 25 MPa), in particular from 10 to 220 bar absolute (1 to 22 MPa) and specifically from 15 to 200 bar absolute (1.5 to 20 MPa). The hydrogenation can be carried out in a variety of reactors known for this purpose.

The hydrogenation step can be carried out as a batch, semi-continuous or continuous process.

Finally, in step (vi.1) the compound of formula (IA) or one or more stereoisomers thereof or a mixture containing the compound of formula (IA) or one or more stereoisomers thereof is isolated from the reaction product of the hydrogenation. This isolation can be carried out by usual means of the art, such as distillative, extractive or chromatographic methods.

For instance, the hydrogenation product of the above-described step (v.1.2) is subjected to a fractional distillation and one or more fractions containing the compound (IA) or stereoisomers thereof or mixtures of stereoisomers thereof are isolated. Preferably, the fractionation is carried out at reduced pressure, e.g. at 0.1 to 500 mbar, preferably at 0.1 to 100 mbar, in particular at 0.1 to 10 mbar and specifically at 0.1 to 5 mbar, e.g. at 0.5 to 2 mbar. Fractions containing the compound (IA) or stereoisomers thereof or mixtures of stereoisomers thereof can be identified by usual means, such as GC/MS and/or NMR. Usually they have a boiling point of ca. 80-90° C. at 5 to 15 mbar, e.g. of 85° C. at 8 mbar.

If desired, the one or more fractions containing the compound (IA) or stereoisomers thereof or mixtures of stereoisomers thereof can be resubmitted to one or more further purification methods, e.g. to one or more (further) fractional distillations or chromatographic methods, such as classical column chromatography, flash chromatography, MPLC or preparative HPLC, in order to further enrich or purify them. Other methods for isolating the compound of formula (IA) or one or more stereoisomers thereof or a mixture containing the compound of formula (IA) or one or more stereoisomers thereof are the chromatographic separation of the products contained in the hydrogenation product of the above-described step (v.1.2), such as column chromatography, flash chromatography, MPLC or preparative HPLC.

Instead of carrying out steps (iv.1), (v.1.2) and (vi.1.), step (iv.1) can be skipped and the bottom fraction of the distillation step (iii) can be directly subjected to a hydrogenation process [step (iv.2)]. The hydrogenation conditions correspond to those described in context with step (v.1.2). Isolation of the compound (IA), of one or more stereoisomers thereof or of a mixture containing the compound of formula (IA) or one or more stereoisomers thereof in step (v.2) can be carried out in analogy to step (vi.1).

Since the high boiling components of the bottom fraction of the distillation step (iii) can however contaminate the hydrogenation catalyst and reduce its activity, it is preferred to apply distillation step (iv.1) and introduce the head product of this step into the hydrogenation reaction. Thus, the reaction sequence (iii)→(iv.1)→(v.1.2)→(vi.1) is preferred over the sequence (iii)→(iv.2)→(v.2).

While chromatographic separation yields the compounds (I) or stereoisomers thereof in high purity and also allows separation of enantiomers if a suitable chiral stationary phase is used, it is more suitable for the production of rather small quantities.

As it has however advantageously turned out, essentially all fractions containing one or more compounds of formula (I) or one or more stereoisomers thereof obtained in the separation step included in steps (v.1.1), (vi.1) or (v.2), in particular all fractions obtained in the fractional distillation step described above in context with the separation step included in steps (v.1.1), (vi.1) or (v.2), are suitable for the purpose of the present invention. "Essentially" relates to the fact that in some instances, the separation process might yields fractions which in addition to one or more compounds (I) or stereoisomer(s) thereof contain other compounds ("impurities"). Such compounds ("impurities") are often other by-products of the aldol condensation and/or hydrogenation of step (i) or (ii). Examples of such by-products are 2,4-diethyloctanal and 2,4-diethyloctanol. These fractions can be used, too, as long as the impurities do not have a significant detrimental effect on the scent of the compounds (I) or stereoisomers thereof or have any other undesired property. This can be tested by a person skilled in the art. The presence of 2,4-diethyloctanal and/or 2,4-diethyloctanol, for instance, does not have any negative impact.

Thus, for the production of the compound (IA) or stereoisomers thereof on an industrial scale, less complex separation methods are sufficient, and the compound of formula (IA) or one or more stereoisomers thereof or a mixture containing the compound of formula (IA) or one or more stereoisomers thereof can for example be isolated from the reaction product of the hydrogenation via fractional distillation. Accordingly, in a particular embodiment, steps (vi.1) or (v.2) are or comprise a fractional distillation of the reaction product of step (v.1.2). or (iv.2)

The same applies to the compounds (I) obtainable via step (v.1.1): less complex separation methods are sufficient, and the compound(s) or one or more stereoisomers thereof can for example be isolated via fractional distillation. Accordingly, in a particular embodiment, step (v.1.1) is or comprises a fractional distillation.

In context with steps (vi.1) and (v.2), "a mixture containing the compound of formula (I) in which $R^1$, $R^2$, $R^3$, $R^4$ and $R^5$ are hydrogen [i.e. compound (IA)] or one or more stereoisomers thereof" as obtained in step (vi.1) or (v.2) relates for example to a mixture which contains, in addition to the compound of formula (IA) or one or more stereoisomers thereof, one or more other components, e.g. one or more of the other compounds ("impurities") mentioned above. Such compounds ("impurities") are often other by-products of the aldol condensation and/or hydrogenation of step (i) or (ii). As said, examples of such by-products are 2,4-diethyloctanal and 2,4-diethyloctanol. Alternatively or additionally, the mixture may contain one or more solvents as other components, especially if the separation or purification step includes a chromatographic or extractive method. Such other components are however only acceptable as long as they do not have a significant detrimental effect on the scent of the compound (IA) or its stereoisomers or have any other undesired property. Otherwise they are removed from the mixture or their amount is reduced to such an extent that they do not disturb the desired properties of the compound (IA) or its stereoisomers. The mixture may principally also comprise minor amounts of one or more compounds (I) as defined in step (v.1.1); i.e. one or more compounds (IB) to (IH), in particular (IB) and/or (IE), specifically (IB), or stereoisomers thereof, especially if the hydrogenation of these compounds in steps (v.1.2) or (iv.2) is not complete. However, hydrogenation in steps (v.1.2) or (iv.2) can be carried out in a way to achieve complete conversion of the compounds (IB) to (IH) into compound (IA) to give mixtures which do not comprise any of compounds (IB) to (IH), e.g. by sufficiently long reaction times and/or by applying sufficiently harsh conditions.

The same applies to the compounds obtained via step (v.1.1); these, too, can contain "impurities" which are acceptable as long as they do not have a significant detrimental effect on the scent of the compounds (I) or have any other undesired property. Otherwise they are removed or their amount is reduced to such an extent that they do not disturb the desired properties of the compounds (I). As already mentioned above, the compounds obtained via step (v.1.1) may comprise the compound (IA), a stereoisomer thereof or a mixture of stereoisomers thereof.

Method A is preferably used to provide compounds (IA). Thus, in a preferred embodiment, method A comprises steps (i) to (iii), (iv.1), (v.1.2) and (vi.1) or steps (i) to (iii), (iv.2) and (v.2). More preferably, method A comprises steps (i) to (iii), (iv.1), (v.1.2) and (vi.1).

Further expediently, a precursor of the compounds of formula (IA) is available as by-product in the production of 2-ethylhexanol from 2-ethylhexenal.

As explained above in context with method A, 2-ethylhexenal is generally produced in an aldol condensation of 2 molecules of n-butyraldehyde; and it is assumed that the compounds of formula (I) or stereoisomers thereof are formed as by-products during said aldol reaction. To be more precise, it is assumed that a minor part of the primary aldol product 2-ethyl-3-hydroxy-hexanal, instead of eliminating water, reacts with a further n-butyraldehyde molecule in an aldol condensation step. The resulting 2,4-diethyl-5-hydroxyoctenal, under the hydrogenation conditions of the conversion of 2-ethylhexenal to 2-ethylhexanol, gives 2,4-diethyloctan-1,5-diol. This can be cyclized to the compound (IA).

Accordingly, in a further aspect, the invention relates to a method for preparing a compound of the formula (I) in which $R^1$, $R^2$, $R^3$, $R^4$ and $R^5$ are hydrogen [i.e. compound (IA)] or a stereoisomer thereof or a mixture of stereoisomers thereof as defined above, comprising (a) subjecting n-butanal to an aldol condensation reaction;
(b) subjecting the reaction product of step (a) containing 2-ethylhexenal to catalytic hydrogenation in the presence of a catalyst suitable for reducing both C—C double bonds to C—C single bonds and aldehyde groups to hydroxy groups;
(c) removing 2-ethylhexanol formed in step (b) by distillation;
(d.1) subjecting the bottom fraction of the distillation in step (c) to a distillation;
(e.1) subjecting the distillation product of step (d.1) [i.e. the head product of the distillation in step (d.1)] to reaction conditions suitable for the cyclization of diols; and
(f.1) isolating the compound of formula (I) in which $R^1$, $R^2$, $R^3$, $R^4$ and $R^5$ are hydrogen [i.e. compound (IA)] or one or more stereoisomers thereof or a mixture containing the compound of formula (I) in which $R^1$, $R^2$, $R^3$, $R^4$ and $R^5$ are hydrogen [i.e. compound (IA)] or one or more stereoisomers thereof;

or (d.2) subjecting the bottom fraction of the distillation in step (c) to reaction conditions suitable for the cyclization of diols;

and (e.2) isolating the compound of formula (I) in which $R^1$, $R^2$, $R^3$, $R^4$ and $R^5$ are hydrogen [i.e. compound (IA)] or one or more stereoisomers thereof or a mixture containing the compound of formula (I) in which $R^1$, $R^2$, $R^3$, $R^4$ and $R^5$ are hydrogen [i.e. compound (IA)] or one or more stereoisomers thereof.

This method is termed method B.

As regards step (a), reference is made to what has been said above in context with step (i) of method A.

In step (b), the reaction product of step (a) containing 2-ethylhexenal is subjected to a catalytic hydrogenation in the presence of a catalyst suitable for reducing both C—C double bonds to C—C single bonds and aldehyde groups to hydroxy groups, so that 2-ethylhexenal is converted into 2-ethylhexanol. Suitable hydrogenation conditions and methods are known in the art and described, for example, in US 2008/0242899, DE-A-2628987 or DE-A-10024542. The hydrogenation is usually carried out in liquid phase, but can also be carried out in the gas phase.

Suitable catalysts are for example nickel, chromium, copper, zinc, manganese or cobalt catalysts or catalysts containing two or more of said metals. Preference is given to Cu, mixed Cu—Cr, mixed Ni—Cu and mixed Ni—Cr catalysts. Among these, preference is given to Cu and Cu—Cr, especially if the hydrogenation is carried out in the gas phase, and to Ni—Cu, especially if the hydrogenation is carried out in the liquid phase.

It can be expedient to use the catalysts in the presence of an additive. Suitable additives are for example the basic oxides or salts of alkali metals or earth alkaline metals, such as the basic oxides or salts of Li, Na, K, Mg or Ca. Suitable basic salts are the hydroxides, carbonates, hydrogencarbonates, amides, $C_1$-$C_4$-alkanolates, such as the methanolates, ethanolates, n-propanolates, isopropanolates, n-butanolates or tert-butanolates, phenolates, or carboxylates, such as acetates or benzoates. Preference is given to the alkali metal or earth alkaline metal hydroxides or carbonates.

The catalyst can be used in supported or unsupported form. Suitable support materials and catalyst forms are explained above in context with method A. For example, $Al_2O_3$, $SiO_2$, in particular amorphous silicon dioxide, barium carbonate, calcium carbonate, magnesium carbonate or diatomaceous earth can be used as support materials. Alternatively, the catalyst can be obtained from reducing the corresponding metal oxide, e.g. Co oxide.

The hydrogenation step can be carried out as a batch, semi-continuous or continuous process.

The reaction temperature is generally from 50 to 200° C., preferably from 80 to 150° C. The hydrogen pressure is generally from 2 to 230 bar absolute (0.2 to 23 MPa), preferably from 5 to 50 bar absolute (0.5 to 5 MPa). The hydrogenation can be carried out in a variety of reactors known for this purpose, such as a serial loop reactor as described in U.S. Pat. No. 5,756,856, but also in simpler reactors, as described for example in DE 2008128. Preference is given to fixed bed reactors, in particular to trickle bed reactors.

The reaction product of the hydrogenation of step (b) containing the hydrogenation product 2-ethylhexanal is then, generally without further purification after separation of the reaction product from the catalyst, subjected to a distillation step (c) in which 2-ethylhexanol is removed. The distillation is generally carried out at atmospheric or reduced pressure, e.g. at from 100 mbar (0.01 MPa) to atmospheric pressure, preferably from 200 to 1000 mbar (0.02 to 0.1 MPa), in particular from 500 to 900 mbar (0.05 to 0.09 MPa), and the external temperature is generally about 10 to 50° C. higher than the boiling point of 2-ethylhexanol at the given pressure, e.g. from 100 to 210° C. The distillation can be carried out in one rectification column or in a series of columns to which the sump or bottom fraction of the previous column is fed.

After all or virtually all 2-ethylhexanol has been distilled of, the bottom fraction (also called sump) of the distillation is subjected to a distillation step (d.1) to separate the lower boiling components of the sump obtained after the distillation in step (c) from the high-boiling components. This distillation step (d.1) is typically carried out at reduced pressure and in particular at a lower pressure than step (iii), e.g. at from 1 to 50 mbar (100 Pa to 5 kPa), preferably at from 1 to 30 mbar (100 Pa to 3 kPa), e.g. at from 5 to 15 mbar (500 Pa to 1500 Pa). The values refer to the head pressure of the distillation apparatus. The temperature depends on the applied vacuum and is generally in the range given above in step (c). The head temperature is generally in the range of 80 to 120° C., specifically at 90 to 100° C. at 5 to 15 mbar head pressure. Generally it is not necessary to carry out the distillation as a rectification, so that simpler distillation apparatuses can be used, provided that vacuum in the required range can be applied. Examples are falling film evaporators or thin film evaporators.

The head product of distillation step (d.1) is then subjected to reaction conditions suitable for the cyclization of diols (step e.1).

As explained above, under the hydrogenation conditions of the conversion of 2-ethylhexenal to 2-ethylhexanol, 2,4- diethyloctan-1,5-diol is formed as by-product. This is the component of the bottom fraction which is to by cyclized to compound (IA).

The cyclization is carried out under conditions suitable for etherifications, especially for the formation of cyclic ethers.

Generally, the cyclization is carried out under acidic conditions, using for example hydrochloric acid, sulfuric acid, acetic acid, trifluoroacetic acid, methanesulfonic acid or p-toluene sulfonic acid or using a polymeric acid, such as an acidic cation exchanger. In a specific embodiment, an acidic cation exchanger is used. The term "acidic cationic exchanger" refers to a cationic exchanger in the H$^+$ form which has acidic groups. The acidic groups are generally sulfonic acid groups; they are generally bonded to a polymer matrix, which can be e.g. gel-like and/or macroporous. Preference is given to styrene (co)polymers containing sulfonic acid groups, specifically to styrene-divinyl benzene copolymers containing sulfonic acid groups. Commercial examples for such cationic exchangers are Lewatit® (Lanxess), Purolite® (The Purolite Company), Dowex® (Dow Chemical Company), Amberlite® (Rohm and Haas Company), Amberlyst® (Rohm and Haas Company). Preferred acidic cation exchangers are: Lewatit® K 1221, Lewatit® K 1461, Lewatit® K 2431, Lewatit® K 2620, Lewatit® K 2621, Lewatit® K 2629, Lewatit® K 2649, Amberlite® FPC 22, Amberlite® FPC 23, Amberlite® IR 120, Amberlyst® 131, Amberlyst® 15, Amberlyst® 31, Amberlyst® 35, Amberlyst® 36, Amberlyst® 39, Amberlyst® 46, Amberlyst® 70, Purolite® SGC650, Purolite® C100H, Purolite® C150H, Dowex® 50X8, Serdolit® red and Nation® NR-50. Specifically, resins of the Amberlyst® brand from Rohm and Haas, and very specifically Amberlyst® 15 is used. Alternatively, the cation exchanger can be a perfluorinated ion exchange resin, sold e.g. under the Nafion® brand of DuPont.

The amount of acidic cation exchanger is not critical and can be chosen freely within wide limits taking into consideration the economic and processing aspect. Accordingly, the reaction can be carried out either in the presence of catalytic amounts or in the presence of large excesses of the acidic cation exchanger. Usually, in batch processes, the acidic cation exchanger is used in an amount of from about 5 up to about 40% by weight, preferably in an amount of from about 5 to about 20% by weight and particularly preferably in an amount of from about 5 to about 15% by weight, in each case based on the weight of the sump. Here, the figures refer to the ready-to-use cation exchanger which is generally pretreated with water and accordingly can comprise amounts of up to about 70% by weight, preferably of about 30 to about 70% by weight and particularly preferably of about 40 to about 70% by weight of water. Preferably however, before use, water contained in the ready to use cation exchanger is removed at least partially. In this case, the above amounts have to be adapted accordingly. In case of continuous or semi-continuous processes, the cation exchanger is used until the desired activity is no longer achieved and is then regenerated.

The reaction is generally carried out at elevated temperature, such as 50 to 200° C., preferably 80 to 150° C., in particular 100 to 140° C. It may be expedient to remove the reaction water. The reaction pressure is not critical, so that generally the reaction is carried out at ambient pressure.

Finally, in step (f.1) the compound of formula (IA) or one or more stereoisomers thereof or a mixture containing the compound of formula (IA) or one or more stereoisomers thereof is isolated from the reaction product of the cyclization reaction. If a cation exchanger has been used, this is generally removed, e.g. by filtration. The isolation can be carried out by usual means of the art, such as distillative, extractive or chromatographic methods. Reference is made to the remarks made in context with step (vi.1) or (v.2) of method A.

Instead of carrying out steps (d.1), (e.1) and (f.1), step (d.1) can be skipped and the bottom fraction of the distillation step (c) can be directly subjected to reaction conditions suitable for the cyclization of diols [step (d.2)]. The cyclization conditions correspond to those described in context with step (e.1). Isolation of the compound (IA), of one or more stereoisomers thereof or of a mixture containing the compound of formula (IA) or one or more stereoisomers thereof in step (e.2) can be carried out in analogy to step (f.1).

Under certain circumstances the high boiling components of the bottom fraction of the distillation step (c) may interfere with the cyclization reaction and it may be expedient to apply distillation step (d.1) and introduce the head product of this step into the cyclization reaction; i.e. to apply the reaction sequence (c)+(d.1)+(e.1)+(f.1). However, in general, the sequence (c)+(d.2)+(e.2) yields sufficiently good results.

As mentioned above, while chromatographic separation yields the compound (IA) or stereoisomers thereof in high purity and also allows separation of enantiomers if a suitable chiral stationary phase is used, it is more suitable for the production of rather small quantities. As it has however advantageously turned out, essentially all fractions containing the compound of formula (IA) or one or more stereoisomers thereof obtained in the separation step included in step (f.1) or (e.2), in particular all fractions obtained in a fractional distillation step in context with the separation step included in steps (f.1) or (e.2), are suitable for the purpose of the present invention. "Essentially" relates to the fact that in some instances, the separation process might yield fractions which in addition to compound (IA) or stereoisomer(s) thereof contain other compounds ("impurities"). These fractions can be used, too, as long as the impurities do not have a significant detrimental effect on the scent of the compound (IA) or stereoisomers thereof or have any other undesired property. This can be tested by a person skilled in the art.

Thus, for the production of the compound (IA) or stereoisomers thereof on an industrial scale, less complex separation methods are sufficient, and the compound of formula (IA) or one or more stereoisomers thereof or a mixture containing the compound of formula (IA) or one or more stereoisomers thereof can for example be isolated from the reaction product of the cyclization via fractional distillation. Accordingly, in a particular embodiment, steps (f.1) or (e.2) are or comprise a fractional distillation of the reaction product of step (e.1) or (d.2).

In context with steps (f.1) or (e.2), "a mixture containing the compound of formula (I) in which $R^1$, $R^2$, $R^3$, $R^4$ and $R^5$ are hydrogen [i.e. compound (IA)] or one or more stereoisomers thereof" as obtained in steps (f.1) or (e.2) relates for example to a mixture which contains, in addition to the compound of formula (IA) or one or more stereoisomers thereof, one or more other components, e.g. one or more of the other compounds ("impurities") mentioned above. As said, such compounds ("impurities") are often other by-products of the aldol condensation and/or hydrogenation of step (a) or (b). Examples of such by-products are 2,4-diethyloctanal and 2,4-diethyloctanol. Alternatively or additionally, the mixture may contain one or more solvents as other components, especially if the separation or purification step includes a chromatographic or extractive method. Such other components are however only acceptable as long as they do not have a significant detrimental effect on the scent of the compound (IA) or its stereoisomers or have any other undesired property. Otherwise they are removed from the mixture or their amount is reduced to such an extent that they do not disturb the desired properties of the compound (IA) or its stereoisomers. The presence of 2,4-diethyloctanal and/or 2,4-diethyloctanol, for instance, does not have any negative impact. Moreover, the mixture may also comprise one or more compounds (IB) to (IH), in particular (IB) and/or (IE), specifically (IB), or one or more stereoisomers thereof. These may be formed as by-product of steps (a) or (b). If at all, these compounds are present in minor amounts, preferably in an overall amount of at most 20% by weight, more preferably of at most 10% by weight, in particular of at most 5% by weight, specifically of at most 2% by weight, very specifically of at most 1% by weight, based on the total weight of compounds (IA) to (IH).

In another aspect, the invention relates to a composition obtainable by the above-described methods A or B of the invention, especially by method A. The composition comprises one or more compounds of formula (I) or one or more stereoisomers thereof.

The composition obtainable by the above method A of the invention is generally understood to be the product obtained in step (v.1.1) or in step (vi.1) or in step (v.2) containing one or more compounds of formula (I) or one or more stereoisomers thereof (in case of steps (vi.1) or (v.2) containing the compound of formula (IA) or one or more stereoisomers thereof or a mixture containing the compound of formula (IA) or one or more stereoisomers thereof). In case of a fractional distillation or chromatographic method used in step (v.1.1) or in step (vi.1) or in step (v.2), it can be one of the fractions obtained in step (v.1.1) or in step (vi.1) or in step (v.2) containing the compound of formula (I) or one or more stereoisomers thereof, or can be the combination of two or more fractions obtained in step (v.1.1) or in step (vi.1) or in step (v.2) containing the compound of formula (I) or one or more stereoisomers thereof, and is in a specific embodiment a combination of all fractions obtained in step (v.1.1) or in step (vi.1) or in step (v.2) containing the compound of formula (I) or one or more stereoisomers thereof, except for those fractions which in addition to compound (I) or its stereoisomer(s) contain other compounds ("impurities") in an amount sufficient to have a significant detrimental effect on the scent of the compound (I) or its stereoisomers and/or any other undesired property.

Preferably, the composition obtainable by the above method A of the invention is the product obtained in step (vi.1) or in step (v.2) containing the compounds of formula (IA) or one or more stereoisomers thereof or a mixture containing the compound of formula (IA) or one or more stereoisomers thereof. In case of a fractional distillation or chromatographic method used in step (vi.1) or in step (v.2), it can be one of the fractions obtained in step (vi.1) or in step (v.2) containing the compound of formula (IA) or one or more stereoisomers thereof, or can be the combination of two or more fractions obtained in step (vi.1) or in step (v.2) containing the compound of formula (IA) or one or more stereoisomers thereof, and is especially a combination of all fractions obtained in step (vi.1) or in step (v.2) containing the compound of formula (IA) or one or more stereoisomers thereof, except for those fractions which in addition to compound (IA) or its stereoisomer(s) contain other compounds ("impurities") in an amount sufficient to have a significant detrimental effect on the scent of the compound (IA) or its stereoisomers and/or any other undesired property.

In particular, the composition obtainable by the above method A of the invention comprises the compound of formula (IA) or one or more stereoisomers thereof in an overall amount of at least 5% by weight, more particularly at least 10% by weight, specifically at least 25% by weight, e.g. at least 50% by weight or at least 70% by weight or at least 80% by weight or at least 90% by weight or at least 95% by weight, based on the total weight of the composition.

The composition obtainable by the above method B of the invention is the product obtained in step (f.1) or in step (e.2) containing the compounds of formula (IA) or one or more stereoisomers thereof or a mixture containing the compound of formula (IA) or one or more stereoisomers thereof. In case of a fractional distillation or chromatographic method used in step (f.1) or in step (e.2), it can be one of the fractions obtained in step (f.1) or in step (e.2) containing the compound of formula (IA) or one or more stereoisomers thereof, or can be the combination of two or more fractions obtained in step (f.1) or in step (e.2) containing the compound of formula (IA) or one or more stereoisomers thereof, and is in a specific embodiment a combination of all fractions obtained in step (f.1) or in step (e.2) containing the compound of formula (IA) or one or more stereoisomers thereof, except for those fractions which in addition to compound (IA) or its stereoisomer(s) contain other compounds ("impurities") in an amount sufficient to have a significant detrimental effect on the scent of the compound (IA) or its stereoisomers and/or any other undesired property.

In particular, the composition obtainable by the above method B of the invention comprises the compound of formula (IA) or one or more stereoisomers thereof in an overall amount of at least 5% by weight, more particularly at least 10% by weight, specifically at least 25% by weight, e.g. at least 50% by weight or at least 70% by weight or at least 80% by weight or at least 90% by weight or at least 95% by weight, based on the total weight of the composition.

As mentioned above, 2,4-diethyloctanal and 2,4-diethyloctanol, which may be formed as by-products in the above-described syntheses, do not have any negative impact on the desired properties of compounds (IA) to (IH). Thus, it is not imperative to separate the desired compounds (I) from 2,4-diethyloctanal and 2,4-diethyloctanol, especially seeing as their separation is rather laborious. Accordingly, in a specific embodiment, the compositions of the invention (i.e. the aroma chemical compositions or the compositions obtained by methods A or B), in addition to the one or more of compounds (IA) to (IH) or one or more stereoisomers thereof, may contain 2,4-diethyloctanal and/or 2,4-diethyloctanol. The latter are contained in minor amounts, such as an overall amount of at most 20% by weight, preferably at most 10% by weight, more preferably at most 5% by weight, in particular at most 2% by weight, specifically at most 1% by weight, based on the total weight of compounds (IA) to (IH), 2,4-diethyloctanal and 2,4-diethyloctanol.

In another aspect, the invention relates to the compound of formula (IA)

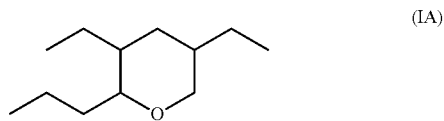

(IA)

and to all stereoisomers thereof, either as single stereoisomers or as a mixture of two or more stereoisomers.

The compound of formula (I) has three stereogenic centers and can thus be present in the form of 8 configurational stereoisomers. These are: (2S,3R,5R)-3,5-diethyl-2-propyl-tetrahydropyran, (2S,3S,5R)-3,5-diethyl-2-propyl-tetrahydropyran, (2S,3R,5S)-3,5-diethyl-2-propyl-tetrahydropyran, (2S,3S,5S)-3,5-diethyl-2-propyl-tetrahydropyran, (2R,3S,5S)-3,5-diethyl-2-propyl-tetrahydropyran, (2R,3R,5S)-3,5-diethyl-2-propyl-tetrahydropyran, (2R,3S,5R)-3,5-diethyl-2-propyl-tetrahydropyran and (2R,3R,5R)-3,5-diethyl-2-propyl-tetrahydropyran.

In one embodiment, the invention relates to (2S,3R,5R)-3,5-diethyl-2-propyl-tetrahydropyran, and to a mixture with 1 or with 2 or with 3 or with 4 or with 5 of the stereoisomers selected from the group consisting of (2S,3S,5R)-3,5-diethyl-2-propyl-tetrahydropyran, (2S,3R,5S)-3,5-diethyl-2-propyl-tetrahydropyran, (2S,3S,5S)-3,5-diethyl-2-propyl-tetrahydropyran, (2R,3S,5S)-3,5-diethyl-2-propyl-tetrahydropyran, (2R,3R,5S)-3,5-diethyl-2-propyl-tetrahydropyran, (2R,3S,5R)-3,5-diethyl-2-propyl-tetrahydropyran and (2R,3R,5R)-3,5-diethyl-2-propyl-tetrahydropyran.

In another embodiment, the invention relates to (2S,3S,5R)-3,5-diethyl-2-propyl-tetrahydropyran, and to a mixture with 1 or with 2 or with 3 or with 4 or with 5 of the stereoisomers selected from the group consisting of (2S,3R,5R)-3,5-diethyl-2-propyl-tetrahydropyran, (2S,3R,5S)-3,5-diethyl-2-propyl-tetrahydropyran, (2S,3S,5S)-3,5-diethyl-2-propyl-tetrahydropyran, (2R,3S,5S)-3,5-diethyl-2-propyl-tetrahydropyran, (2R,3R,5S)-3,5-diethyl-2-propyl-tetrahydropyran, (2R,3S,5R)-3,5-diethyl-2-propyl-tetrahydropyran and (2R,3R,5R)-3,5-diethyl-2-propyl-tetrahydropyran.

In another embodiment, the invention relates to (2S,3R,5S)-3,5-diethyl-2-propyl-tetrahydropyran, and to a mixture with 1 or with 2 or with 3 or with 4 or with 5 of the stereoisomers selected from the group consisting of (2S,3R,5R)-3,5-diethyl-2-propyl-tetrahydropyran, (2S,3S,5R)-3,5-diethyl-2-propyl-tetrahydropyran, (2S,3S,5S)-3,5-diethyl-2-propyl-tetrahydropyran, (2R,3S,5S)-3,5-diethyl-2-propyl-tetrahydropyran, (2R,3R,5S)-3,5-diethyl-2-propyl-tetrahydropyran, (2R,3S,5R)-3,5-diethyl-2-propyl-tetrahydropyran and (2R,3R,5R)-3,5-diethyl-2-propyl-tetrahydropyran.

In another embodiment, the invention relates to (2S,3S,5S)-3,5-diethyl-2-propyl-tetrahydropyran, and to a mixture with 1 or with 2 or with 3 or with 4 or with 5 of the stereoisomers selected from the group consisting of (2S,3R,5R)-3,5-diethyl-2-propyl-tetrahydropyran, (2S,3S,5R)-3,5-diethyl-2-propyl-tetrahydropyran, (2S,3R,5S)-3,5-diethyl-2-propyl-tetrahydropyran, (2R,3S,5S)-3,5-diethyl-2-propyl-tetrahydropyran, (2R,3R,5S)-3,5-diethyl-2-propyl-tetrahydropyran, (2R,3S,5R)-3,5-diethyl-2-propyl-tetrahydropyran and (2R,3R,5R)-3,5-diethyl-2-propyl-tetrahydropyran.

In another embodiment, the invention relates to (2R,3S,5S)-3,5-diethyl-2-propyl-tetrahydropyran, and to a mixture with 1 or with 2 or with 3 or with 4 or with 5 of the stereoisomers selected from the group consisting of (2S,3R,5R)-3,5-diethyl-2-propyl-tetrahydropyran, (2S,3S,5R)-3,5-diethyl-2-propyl-tetrahydropyran, (2S,3R,5S)-3,5-diethyl-2-propyl-tetrahydropyran, (2S,3S,5S)-3,5-diethyl-2-propyl-tetrahydropyran, (2R,3R,5S)-3,5-diethyl-2-propyl-tetrahydropyran, (2R,3S,5R)-3,5-diethyl-2-propyl-tetrahydropyran and (2R,3R,5R)-3,5-diethyl-2-propyl-tetrahydropyran.

In another embodiment, the invention relates to (2R,3R,5S)-3,5-diethyl-2-propyl-tetrahydropyran, and to a mixture with 1 or with 2 or with 3 or with 4 or with 5 of the stereoisomers selected from the group consisting of (2S,3R,5R)-3,5-diethyl-2-propyl-tetrahydropyran, (2S,3S,5R)-3,5-diethyl-2-propyl-tetrahydropyran, (2S,3R,5S)-3,5-diethyl-2-propyl-tetrahydropyran, (2S,3S,5S)-3,5-diethyl-2-propyl-tetrahydropyran, (2R,3S,5S)-3,5-diethyl-2-propyl-tetrahydropyran, (2R,3S,5R)-3,5-diethyl-2-propyl-tetrahydropyran and (2R,3R,5R)-3,5-diethyl-2-propyl-tetrahydropyran.

In another embodiment, the invention relates to (2R,3S,5R)-3,5-diethyl-2-propyl-tetrahydropyran, and to a mixture with 1 or with 2 or with 3 or with 4 or with 5 of the stereoisomers selected from the group consisting of (2S,3R,5R)-3,5-diethyl-2-propyl-tetrahydropyran, (2S,3S,5R)-3,5-diethyl-2-propyl-tetrahydropyran, (2S,3R,5S)-3,5-diethyl-2-propyl-tetrahydropyran, (2S,3S,5S)-3,5-diethyl-2-propyl-tetrahydropyran, (2R,3S,5S)-3,5-diethyl-2-propyl-tetrahydropyran, (2R,3R,5S)-3,5-diethyl-2-propyl-tetrahydropyran and (2R,3R,5R)-3,5-diethyl-2-propyl-tetrahydropyran.

In another embodiment, the invention relates to (2R,3R,5R)-3,5-diethyl-2-propyl-tetrahydropyran, and to a mixture with 1 or with 2 or with 3 or with 4 or with 5 of the stereoisomers selected from the group consisting of (2S,3R,5R)-3,5-diethyl-2-propyl-tetrahydropyran, (2S,3S,5R)-3,5-diethyl-2-propyl-tetrahydropyran, (2S,3R,5S)-3,5-diethyl-2-propyl-tetrahydropyran, (2S,3S,5S)-3,5-diethyl-2-propyl-tetrahydropyran, (2R,3S,5S)-3,5-diethyl-2-propyl-tetrahydropyran, (2R,3R,5S)-3,5-diethyl-2-propyl-tetrahydropyran and (2R,3S,5R)-3,5-diethyl-2-propyl-tetrahydropyran.

In a particular embodiment, the mixture of stereoisomers of compound (I) is selected from the group consisting of mixtures M.1 to M.238 as listed in Table 1, where A is (2S,3R,5R)-3,5-diethyl-2-propyl-tetrahydropyran, B is (2S,3S,5R)-3,5-diethyl-2-propyl-tetrahydropyran, C is (2S,3R,5S)-3,5-diethyl-2-propyl-tetrahydropyran, D is (2S,3S,5S)-3,5-diethyl-2-propyl-tetrahydropyran, E is (2R,3S,5S)-3,5-diethyl-2-propyl-tetrahydropyran, F is (2R,3R,5S)-3,5-diethyl-2-propyl-tetrahydropyran, G is (2R,3S,5R)-3,5-diethyl-2-propyl-tetrahydropyran and H is (2R,3R,5R)-3,5-diethyl-2-propyl-tetrahydropyran; and C.1, C.2, C.3, C.4, C.5 and C.6 are components 1, 2, if present 3, if present 4, if present 5 and if present 6 of the mixture of stereoisomers.

TABLE 1

| Mixture | C.1 | C.2 | C.3 | C.4 | C.5 | C.6 |
|---------|-----|-----|-----|-----|-----|-----|
| M.1 | A | B | — | — | — | — |
| M.2 | A | C | — | — | — | — |
| M.3 | A | D | — | — | — | — |
| M.4 | A | E | — | — | — | — |
| M.5 | A | F | — | — | — | — |
| M.6 | A | G | — | — | — | — |
| M.7 | A | H | — | — | — | — |
| M.8 | B | C | — | — | — | — |
| M.9 | B | D | — | — | — | — |
| M.10 | B | E | — | — | — | — |
| M.11 | B | F | — | — | — | — |
| M.12 | B | G | — | — | — | — |
| M.13 | B | H | — | — | — | — |
| M.14 | C | D | — | — | — | — |
| M.15 | C | E | — | — | — | — |
| M.16 | C | F | — | — | — | — |
| M.17 | C | G | — | — | — | — |
| M.18 | C | H | — | — | — | — |
| M.19 | D | E | — | — | — | — |

TABLE 1-continued

| Mixture | C.1 | C.2 | C.3 | C.4 | C.5 | C.6 |
|---|---|---|---|---|---|---|
| M.20 | D | F | — | — | — | — |
| M.21 | D | G | — | — | — | — |
| M.22 | D | H | — | — | — | — |
| M.23 | E | F | — | — | — | — |
| M.24 | E | G | — | — | — | — |
| M.25 | E | H | — | — | — | — |
| M.26 | F | G | — | — | — | — |
| M.27 | F | H | — | — | — | — |
| M.28 | G | H | — | — | — | — |
| M.29 | A | B | C | — | — | — |
| M.30 | A | B | D | — | — | — |
| M.31 | A | B | E | — | — | — |
| M.32 | A | B | F | — | — | — |
| M.33 | A | B | G | — | — | — |
| M.34 | A | B | H | — | — | — |
| M.35 | A | C | D | — | — | — |
| M.36 | A | C | E | — | — | — |
| M.37 | A | C | F | — | — | — |
| M.38 | A | C | G | — | — | — |
| M.39 | A | C | H | — | — | — |
| M.40 | A | D | E | — | — | — |
| M.41 | A | D | F | — | — | — |
| M.42 | A | D | G | — | — | — |
| M.43 | A | D | H | — | — | — |
| M.44 | A | E | F | — | — | — |
| M.45 | A | E | G | — | — | — |
| M.46 | A | E | H | — | — | — |
| M.47 | A | F | G | — | — | — |
| M.48 | A | F | H | — | — | — |
| M.49 | A | G | H | — | — | — |
| M.50 | B | C | D | — | — | — |
| M.51 | B | C | E | — | — | — |
| M.52 | B | C | F | — | — | — |
| M.53 | B | C | G | — | — | — |
| M.54 | B | C | H | — | — | — |
| M.55 | B | D | E | — | — | — |
| M.56 | B | D | F | — | — | — |
| M.57 | B | D | G | — | — | — |
| M.58 | B | D | H | — | — | — |
| M.59 | B | E | F | — | — | — |
| M.60 | B | E | G | — | — | — |
| M.61 | B | E | H | — | — | — |
| M.62 | B | F | G | — | — | — |
| M.63 | B | F | H | — | — | — |
| M.64 | B | G | H | — | — | — |
| M.65 | C | D | E | — | — | — |
| M.66 | C | D | F | — | — | — |
| M.67 | C | D | G | — | — | — |
| M.68 | C | D | H | — | — | — |
| M.69 | C | E | F | — | — | — |
| M.70 | C | E | G | — | — | — |
| M.71 | C | E | H | — | — | — |
| M.72 | C | F | G | — | — | — |
| M.73 | C | F | H | — | — | — |
| M.74 | C | G | H | — | — | — |
| M.75 | D | E | F | — | — | — |
| M.76 | D | E | G | — | — | — |
| M.77 | D | E | H | — | — | — |
| M.78 | D | F | G | — | — | — |
| M.79 | D | F | H | — | — | — |
| M.80 | D | G | H | — | — | — |
| M.81 | E | F | G | — | — | — |
| M.82 | E | F | H | — | — | — |
| M.83 | E | G | H | — | — | — |
| M.84 | F | G | H | — | — | — |
| M.85 | A | B | C | D | — | — |
| M.86 | A | B | C | E | — | — |
| M.87 | A | B | C | F | — | — |
| M.88 | A | B | C | G | — | — |
| M.89 | A | B | C | H | — | — |
| M.90 | A | B | D | E | — | — |
| M.91 | A | B | D | F | — | — |
| M.92 | A | B | D | G | — | — |
| M.93 | A | B | D | H | — | — |
| M.94 | A | B | E | F | — | — |
| M.95 | A | B | E | G | — | — |
| M.96 | A | B | E | H | — | — |
| M.97 | A | B | F | G | — | — |
| M.98 | A | B | F | H | — | — |
| M.99 | A | B | G | H | — | — |
| M.100 | A | C | D | E | — | — |
| M.101 | A | C | D | F | — | — |
| M.102 | A | C | D | G | — | — |
| M.103 | A | C | D | H | — | — |
| M.104 | A | C | E | F | — | — |
| M.105 | A | C | E | G | — | — |
| M.106 | A | C | E | H | — | — |
| M.107 | A | C | F | G | — | — |
| M.108 | A | C | F | H | — | — |
| M.109 | A | C | G | H | — | — |
| M.110 | A | D | E | F | — | — |
| M.111 | A | D | E | G | — | — |
| M.112 | A | D | E | H | — | — |
| M.113 | A | D | F | G | — | — |
| M.114 | A | D | F | H | — | — |
| M.115 | A | D | G | H | — | — |
| M.116 | A | E | F | G | — | — |
| M.117 | A | E | F | H | — | — |
| M.118 | A | E | G | H | — | — |
| M.119 | A | F | G | H | — | — |
| M.120 | B | C | D | E | — | — |
| M.121 | B | C | D | F | — | — |
| M.122 | B | C | D | G | — | — |
| M.123 | B | C | D | H | — | — |
| M.124 | B | C | E | F | — | — |
| M.125 | B | C | E | G | — | — |
| M.126 | B | C | E | H | — | — |
| M.127 | B | C | F | G | — | — |
| M.128 | B | C | F | H | — | — |
| M.129 | B | C | G | H | — | — |
| M.130 | B | D | E | F | — | — |
| M.131 | B | D | E | G | — | — |
| M.132 | B | D | E | H | — | — |
| M.133 | B | D | F | G | — | — |
| M.134 | B | D | F | H | — | — |
| M.135 | B | D | G | H | — | — |
| M.136 | B | E | F | G | — | — |
| M.137 | B | E | F | H | — | — |
| M.138 | B | E | G | H | — | — |
| M.139 | B | F | G | H | — | — |
| M.140 | C | D | E | F | — | — |
| M.141 | C | D | E | G | — | — |
| M.142 | C | D | E | H | — | — |
| M.143 | C | D | F | G | — | — |
| M.144 | C | D | F | H | — | — |
| M.145 | C | D | G | H | — | — |
| M.146 | C | E | F | G | — | — |
| M.147 | C | E | F | H | — | — |
| M.148 | C | E | G | H | — | — |
| M.149 | C | F | G | H | — | — |
| M.150 | D | E | F | G | — | — |
| M.151 | D | E | F | H | — | — |
| M.152 | D | E | G | H | — | — |
| M.153 | D | F | G | H | — | — |
| M.154 | E | F | G | H | — | — |
| M.155 | A | B | C | D | E | — |
| M.156 | A | B | C | D | F | — |
| M.157 | A | B | C | D | G | — |
| M.158 | A | B | C | D | H | — |
| M.159 | A | B | C | E | F | — |
| M.160 | A | B | C | E | G | — |
| M.161 | A | B | C | E | H | — |
| M.162 | A | B | C | F | G | — |
| M.163 | A | B | C | F | H | — |
| M.164 | A | B | C | G | H | — |
| M.165 | A | B | D | E | F | — |
| M.166 | A | B | D | E | G | — |
| M.167 | A | B | D | E | H | — |
| M.168 | A | B | D | F | G | — |
| M.169 | A | B | D | F | H | — |
| M.170 | A | B | D | G | H | — |
| M.171 | A | B | E | F | G | — |
| M.172 | A | B | E | F | H | — |
| M.173 | A | B | E | G | H | — |
| M.174 | A | B | F | G | H | — |
| M.175 | A | C | D | E | F | — |

TABLE 1-continued

| Mixture | C.1 | C.2 | C.3 | C.4 | C.5 | C.6 |
|---------|-----|-----|-----|-----|-----|-----|
| M.176 | A | C | D | E | G | — |
| M.177 | A | C | D | E | H | — |
| M.178 | A | C | D | F | G | — |
| M.179 | A | C | D | F | H | — |
| M.180 | A | C | D | G | H | — |
| M.181 | A | C | E | F | G | — |
| M.182 | A | C | E | F | H | — |
| M.183 | A | C | E | G | H | — |
| M.184 | A | C | F | G | H | — |
| M.185 | A | D | E | F | G | — |
| M.186 | A | D | E | F | H | — |
| M.187 | A | D | E | G | H | — |
| M.188 | A | D | F | G | H | — |
| M.189 | A | E | F | G | H | — |
| M.190 | B | C | D | E | F | — |
| M.191 | B | C | D | E | G | — |
| M.192 | B | C | D | E | H | — |
| M.193 | B | C | D | F | G | — |
| M.194 | B | C | D | F | H | — |
| M.195 | B | C | D | G | H | — |
| M.196 | B | C | E | F | G | — |
| M.197 | B | C | E | F | H | — |
| M.198 | B | C | E | G | H | — |
| M.199 | B | C | F | G | H | — |
| M.200 | B | D | E | F | G | — |
| M.201 | B | D | E | F | H | — |
| M.202 | B | D | E | G | H | — |
| M.203 | B | D | F | G | H | — |
| M.204 | B | E | F | G | H | — |
| M.205 | C | D | E | F | G | — |
| M.206 | C | D | E | F | H | — |
| M.207 | C | D | E | G | H | — |
| M.208 | C | D | F | G | H | — |
| M.209 | C | E | F | G | H | — |
| M.210 | D | E | F | G | H | — |
| M.211 | A | B | C | D | E | F |
| M.212 | A | B | C | D | E | G |
| M.213 | A | B | C | D | E | H |
| M.214 | A | B | C | D | F | G |
| M.215 | A | B | C | D | F | H |
| M.216 | A | B | C | D | G | H |
| M.217 | A | B | C | E | F | G |
| M.218 | A | B | C | E | F | H |
| M.219 | A | B | C | E | G | H |
| M.220 | A | B | C | F | G | H |
| M.221 | A | B | D | E | F | G |
| M.222 | A | B | D | E | F | H |
| M.223 | A | B | D | E | G | H |
| M.224 | A | B | D | F | G | H |
| M.225 | A | B | E | F | G | H |
| M.226 | A | C | D | E | F | G |
| M.227 | A | C | D | E | F | H |
| M.228 | A | C | D | E | G | H |
| M.229 | A | C | D | F | G | H |
| M.230 | A | C | E | F | G | H |
| M.231 | A | D | E | F | G | H |
| M.232 | B | C | D | E | F | G |
| M.233 | B | C | D | E | F | H |
| M.234 | B | C | D | E | G | H |
| M.235 | B | C | D | F | G | H |
| M.236 | B | C | E | F | G | H |
| M.237 | B | D | E | F | G | H |
| M.238 | C | D | E | F | G | H |

In a mixture of two stereoisomers, the single stereoisomer is preferably present in a relative amount of from 5 to 95 mol-%, more preferably from 10 to 90 mol-%, in particular from 20 to 80 mol-%, more particularly from 30 to 70 mol-% and specifically from 40 to 60 mol-%, the sum of the percentages in which the two stereoisomers are present yielding of course 100 mol-%.

In a mixture of three stereoisomers, the single stereoisomer is generally present in a relative amount of from 5 to 90 mol-%, preferably from 10 to 80 mol-%, more preferably from 20 to 60 mol-% and in particular from 25 to 40 mol-%, the sum of the percentages in which the three stereoisomers are present yielding of course 100 mol-%.

In a mixture of four stereoisomers, the single stereoisomer is generally present in a relative amount of from 2 to 94 mol-%, preferably from 5 to 85 mol-%, more preferably from 10 to 70 mol-%, in particular from 15 to 55 mol-% and specifically from 15 to 40 mol-%, the sum of the percentages in which the four stereoisomers are present yielding of course 100 mol-%.

In a mixture of five stereoisomers, the single stereoisomer is generally present in a relative amount of from 1 to 96 mol-%, preferably from 5 to 80 mol-%, more preferably from 10 to 60 mol-%, in particular from 15 to 40 mol-% and specifically from 17 to 32 mol-%, the sum of the percentages in which the five stereoisomers are present yielding of course 100 mol-%.

In a mixture of six stereoisomers, the single stereoisomer is generally present in a relative amount of from 1 to 95 mol-%, preferably from 2 to 90 mol-%, more preferably from 5 to 75 mol-%, in particular from 10 to 50 mol-% and specifically from 15 to 25 mol-%, the sum of the percentages in which the five stereoisomers are present yielding of course 100 mol-%.

In another embodiment, the invention relates to a stereoisomer of the compound of formula (IA), selected from the group consisting of
  t-3,c-5-diethyl-r-2-propyl-tetrahydropyran,
  t-3,t-5-diethyl-r-2-propyl-tetrahydropyran,
  c-3,t-5-diethyl-r-2-propyl-tetrahydropyran, and
  c-3,c-5-diethyl-r-2-propyl-tetrahydropyran,
or to a mixture of two or three of these diastereomers.

As already explained above, in this relative nomenclature the substituent with the highest priority (here propyl) is defined as reference group ("r") and the two ethyl groups are defined relative to this propyl reference group as cis ("c") or trans ("t").

In yet another embodiment, the invention relates to a mixture of the four following stereoisomers of the compound of formula (IA) according to claim 25:
  t-3,c-5-diethyl-r-2-propyl-tetrahydropyran (IA.1),
  t-3,t-5-diethyl-r-2-propyl-tetrahydropyran (IA.2),
  c-3,t-5-diethyl-r-2-propyl-tetrahydropyran (IA.3), and
  c-3,c-5-diethyl-r-2-propyl-tetrahydropyran (IA.4),
where in the mixture of the four stereoisomers these are contained in following amounts:
  (IA.1): 10 to 25% by weight;
  (IA.2): 20 to 35% by weight;
  (IA.3): 25 to 40% by weight;
  (IA.4): 10 to 32% by weight;
in each case relative to the overall amount of the four stereoisomers (IA.1), (IA.2), (IA.3) and (IA.4) (the amounts of the four stereoisomers add to 100%); where in particular not all four stereoisomers are present in an amount of 25% by weight
or are contained in following amounts:
  (IA.1): 78 to 88% by weight;
  (IA.2): 0.5 to 3% by weight;
  (IA.3): 5 to 15% by weight;
  (IA.4): 2 to 8% by weight;
in each case relative to the overall amount of the four stereoisomers (IA.1), (IA.2), (IA.3) and (IA.4) (the amounts of the four stereoisomers add to 100%).

Preferably, in the mixture of the four stereoisomers these are contained in following amounts:
  (IA.1): 12 to 23% by weight;
  (IA.2): 24 to 32% by weight;

(IA.3): 30 to 37% by weight;
(IA.4): 12 to 29% by weight;
in each case relative to the overall amount of the four stereoisomers (IA.1), (IA.2), (IA.3) and (IA.4) (the amounts of the four stereoisomers add to 100%);
or are contained in following amounts:
(IA.1): 80 to 85% by weight;
(IA.2): 1 to 2.5% by weight;
(IA.3): 8 to 11% by weight;
(IA.4): 4 to 7% by weight;
in each case relative to the overall amount of the four stereoisomers (IA.1), (IA.2), (IA.3) and (IA.4) (the amounts of the four stereoisomers add to 100%).

Finally, the invention also relates to a mixture containing the compound of formula (IA) or one or more stereoisomers thereof, the compound of formula (IB) or one or more stereoisomers thereof, and optionally also the compound of formula (IE) or one or more stereoisomers thereof. Preferably, the mixture contains the compounds (IB) and, if present, (IE) or their stereoisomers in an overall amount of from 1 to 90% by weight, e.g. from 2 to 70% by weight, or from 5 to 50% by weight, or from 10 to 30% by weight, based on the total weight of (IA), (IB) and (IE) (if present).

The invention is illustrated by the following examples.

EXAMPLES

1. Preparation

A Preparation of 3,5-diethyl-2-propyl-tetrahydropyran using the synthesis of 2-ethylhexanal 1.1 Aldol Condensation 2-Ethylhexenal was prepared via aldol condensation of n-butanal using an aqueous 2% by weight NaOH solution (relative to the weight of the solution) as catalyst. 500 g of n-butanal were mixed with 500 g of aqueous 2% by weight NaOH and heated to 90° C. under vigorous stirring. After 30 min the reaction mixture was allowed to stand and separate into two layers.

1.2 Hydrogenation

The organic layer obtained in 1.1 was separated and transferred to a trickle bed reactor with a solid bed catalyst of Pd, $Na_2O$ and $Fe_2O_3$ on alumina. Hydrogenation was carried out at 80° C. and 20 bar of hydrogen pressure.

1.3 Distillation

After pressure release, the reaction product of 1.2 was transferred to a first distillation column operated at 850 mbar and an external temperature of 180° C. (bottom of the column) to 128° C. (top of the column). 2-Ethylhexanal was removed as sidestream and the high-boiling bottom product was transferred to a second column operated at ambient pressure and a temperature of from 209° C. (bottom of the column) to 162° C. (top of the column). The light-boiling head product of the column was then recirculated in the first column.

1.4 Distillation of the Bottom Product of Step 1.3

The bottom product of step 1.3 was subjected to distillation in a thin-film evaporator. The head product obtained at 95° C. head temperature and 10 mbar head pressure was used in the following hydrogenation step.

1.5.1 Hydrogenation

The head product of step 1.4 was subjected to hydrogenation using palladium on carbon as catalyst. Hydrogenation was carried out at 170° C. and 180 bar of hydrogen pressure.

1.6.1 Isolation

The product of 1.5.1 was subjected to a fractional distillation. Fractional distillation was carried out in a Batch column with about 20 theoretical stages at 8 mbar head pressure, reflux ratio 5:1 and 85° C. head temperature.

Characterization of the product:

HRMS: Calculated for $C_{12}H_{24}O$ ($M^+$): 184.18217. Found: 184.18264.

$^1$H NMR: 4 diastereomers: (500 MHz; $CDCl_3$): δ [ppm]=3.9 (dd, 2H), 3.7 (dd, 1H), 3.6 (tt, 2H), 3.5 (dd, 1H), 3.1 (t, 1H), 3.0-2.8 (m, 5H), 2.3-0.8 (m, 84H).

1.5.2 Alternative hydrogenation—continuous process with Pd/C

The head product of step 1.4 was subjected to hydrogenation using palladium on carbon as catalyst (1% Pd). In an apparatus for continuous hydrogenation (tubular reactor) were placed 190 ml of catalyst (molded form/split). Hydrogenation was carried out at 190° C. and 50 bar. The head product of step 1.4 was added at a rate of 38 g/h; load 0.2 $kg/l_{catalyst}$·h. The charge/reflux ratio was 1:20; hydrogen was added at 50 NL/h.

GC analysis revealed that compound (IA) was obtained in the form of its four diastereomers in following ratios:
(IA.1): 21.1% by weight;
(IA.2): 29.7% by weight;
(IA.3): 34.9% by weight;
(IA.4): 14.2% by weight.

1.6.2 Isolation

The product of 1.5.2 was subjected to a fractional distillation in analogy to step 1.6.1.

1.5.3 Alternative Hydrogenation—Continuous Process with Cu/Ni

The head product of step 1.4 was subjected to hydrogenation using a Cu/Ni catalyst with following composition: 21.5% NiO, 7.5% copper oxide, 2.0% manganese oxide, silica as carrier. In an apparatus for continuous hydrogenation (tubular reactor) were placed 190 ml of the catalyst and the latter was activated in a nitrogen/hydrogen atmosphere at 280° C. Hydrogenation was carried out at 190° C. and 50 bar. The head product of step 1.4 was added at a rate of 38 g/h; load 0.2 $kg/l_{catalyst}$*h. The charge/reflux ratio was 1:23; hydrogen was added at 50 NL/h.

GC analysis revealed that compound (IA) was obtained in the form of its four diastereomers in following ratios:
(IA.1): 14.0% by weight;
(IA.2): 25.9% by weight;
(IA.3): 32.9% by weight;
(IA.4): 27.2% by weight.

1.6.3 Isolation

The product of 1.5.3 was subjected to a fractional distillation in analogy to step 1.6.1.

1.5.4 Alternative Hydrogenation—Batch Process with Pd/C 100 g of the head product of step 1.4 was subjected to hydrogenation using palladium on carbon as catalyst (5% Pd). In a stirred autoclave were placed 5 g of catalyst and 100 g of the high-boiling bottom product of 1.3. Hydrogenation was carried out at 140° C. and 60 bar for 24 h.

GC analysis revealed that compound (IA) was obtained in the form of its four diastereomers in following ratios:
(IA.1): 20.8% by weight;
(IA.2): 27.5% by weight;
(IA.3): 31.5% by weight;
(IA.4): 20.1% by weight.

1.6.4 Isolation

The product of 1.5.4 was subjected to a fractional distillation in analogy to step 1.6.1.

B Preparation of 3,5-diethyl-2-propyl-dihydropyran Using the Synthesis of 2-ethylhexanal 1.5 g of the head product of step 1.4 were subjected to column chromatography (stationary phase: 40 g silica; eluent: 100% cyclohexane for 11 min, within 1 min gradual change to 100% ethyl acetate). Fraction A contained a mixture of compounds (IB) and (IE) in a ratio of 3:1 (70% purity). Fraction B contained compound (IB) (purity: 90%).

C Preparation of 3,5-diethyl-2-propyl-tetrahydropyran Using the Synthesis of 2-ethylhexanol In a 3-necked flask with reflux condenser and thermometer, 50 g of Amberlyst® 15 cation exchange resin from Rohm&Haas Company were added to 500 g of the distillation sump of the 2-ethylhexanol synthesis via reduction of 2-ethylhexenal and the mixture was stirred at 120° C. for 196 h. The cation exchange resin was separated from the reaction mixture by filtration. GC analysis revealed that the compound (IA) was obtained in the form of its four diastereomers in following ratios:

(IA.1): 82.9% by weight;
(IA.2): 1.9% by weight;
(IA.3): 9.8% by weight;
(IA.4): 5.4% by weight.

The filtrate was distilled in a batch column with ca 20 theoretical plates with a head pressure of 10 mbar. The maximum sump temperature was 120° C., the reflux ratio 5:1.

2. Olfactory Assessment

In order to test the quality and intensity of the odor of the compound obtained in the preparation examples, scent strip tests were performed. For this purpose, strips of absorbent paper were dipped into a solution containing 1 to 10% by weight solution of the compound to be tested in ethanol. After evaporation of the solvent (about 30 sec.) the scent impression was olfactively evaluated by a trained perfumer. The results are summarized in Table 1.

TABLE 1

Results of the scent tests

| Example no. | Compound | Odor Description |
|---|---|---|
| 1* | (IA) | minty, fresh, green, herbal, woody, dried fruits |
| 2** | (IB) + (IE) weight ratio 3:1; purity 70% or (IB) purity 90% | herbal, woody, dried fruits, fatty |

*Product of examples 1.6.1, 1.6.2, 1.6.3, 1.6.4 or C. No significant olfactory difference between the products of examples 1.6.1, 1.6.2, 1.6.3, 1.6.4 and C.
**Product of example B; fractions A and B. No significant olfactory difference between fractions A and B of example B.

We claim:

1. An aroma chemical composition, comprising a compound of formula (I)

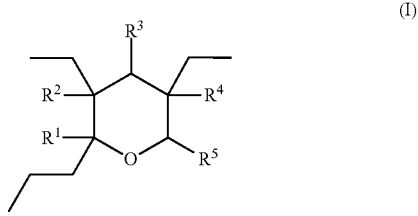

wherein $R^1$, $R^2$, $R^3$, $R^4$ and $R^5$ are hydrogen; or $R^1$ and $R^2$, together with the carbon atoms to which they are bound, form a C—C double bond and $R^3$, $R^4$ and $R^5$ are hydrogen; or $R^2$ and $R^3$, together with the carbon atoms to which they are bound, form a C—C double bond and $R^1$, $R^4$ and $R^5$ are hydrogen; or $R^3$ and $R^4$, together with the carbon atoms to which they are bound, form a C—C double bond and $R^1$, $R^2$ and $R^5$ are hydrogen; or $R^4$ and $R^5$, together with the carbon atoms to which they are bound, form a C—C double bond and $R^1$, $R^2$ and $R^3$ are hydrogen; or $R^1$ and $R^2$, together with the carbon atoms to which they are bound, form a C—C double bond, $R^3$ and $R^4$, together with the carbon atoms to which they are bound, form a C—C double bond, and R⁵ is hydrogen; or R¹ and R², together with the carbon atoms to which they are bound, form a C—C double bond, R⁴ and R⁵, together with the carbon atoms to which they are bound, form a C—C double bond, and R³ is hydrogen; or R² and R³, together with the carbon atoms to which they are bound, form a C—C double bond, R⁴ and R⁵, together with the carbon atoms to which they are bound, form a C—C double bond, and R¹ is hydrogen;

or a stereoisomer thereof, or a mixture of different compounds of formula (I), or a mixture of stereoisomers of a compound of formula (I) or of different compounds of formula (I).

2. The aroma chemical composition according to claim 1, comprising
a compound of formula (I), or a stereoisomer thereof, or a mixture of different compounds of formula (I), or a mixture of stereoisomers of a compound of formula (I) or of different compounds of formula (I); and
at least one further aroma chemical and/or at least one non-aroma chemical component.

3. The aroma chemical composition according to claim 1, comprising the compound of formula (IA), which is a compound of formula (I), wherein R¹, R², R³, R⁴ and R⁵ are hydrogen; or the compound of formula (IB), which is a compound of formula (I) wherein R¹ and R², together with the carbon atoms to which they are bound, form a C—C double bond and R³, R⁴ and R⁵ are hydrogen; or the compound of formula (IE), which is a compound of formula (I) wherein R⁴ and R⁵, together with the carbon atoms to which they are bound, form a C—C double bond and R¹, R² and R³ are hydrogen; or a mixture of two or of all three of the compounds of formulae (IA), (IB) and (IE); or a stereoisomer of a compound of formula (IA), (IB) or (IE); or a mixture of stereoisomers of one of the compounds of formula (IA), (IB) or (IE); or a mixture of stereoisomers of two or of all three of the compounds of formula (IA), (IB) and (IE)

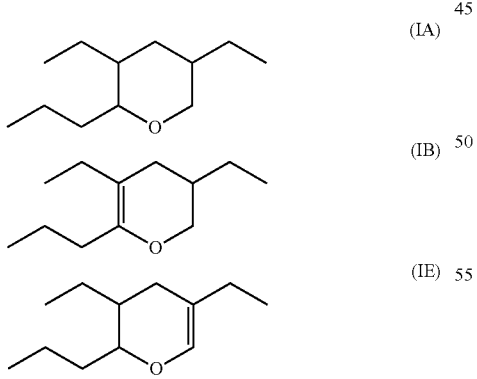

and comprising in particular the compound of formula (IA); or the compound of formula (IB); or a mixture of the compounds of formula (IA) and (IB); or a stereoisomer of a compound of formula (IA) or (IB); or a mixture of stereoisomers of one of the compounds of formula (IA) or (IB); or a mixture of stereoisomers of the compounds of formula (IA) and (IB).

4. The aroma chemical composition according to claim 1, containing as compound of formula (I) the compound of the formula (IA)

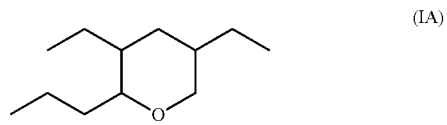

or a stereoisomer thereof or a mixture of different stereoisomers thereof, optionally in admixture with at least one of: the compound of the formula (IB), a stereoisomer thereof, the compound of the formula (IE), or a stereoisomer thereof

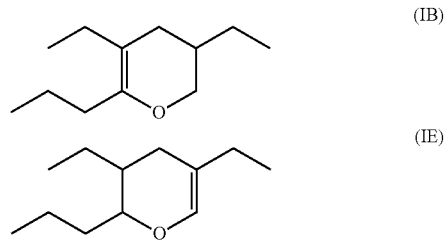

where in case that the composition contains the compounds of formulae (IB) and/or (IE) or one or more stereoisomers thereof, these are contained in an overall amount of at most 20% by weight, preferably at most 10% by weight, relative to the overall weight of compounds of formulae (IA), (IB) and (IE).

5. The aroma chemical composition according to claim 1, containing as compound of formula (I) the compound of formula (IB) or the compound of formula (IE) or a mixture thereof

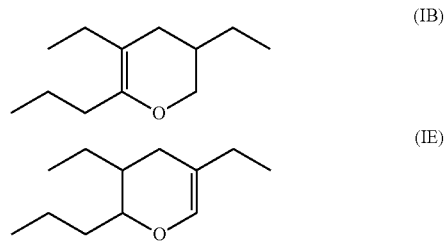

or a stereoisomer of the compound of the formula (IB) or (IE) or a mixture of stereoisomers of the compounds of formula (IB) and/or (IE);
optionally in admixture with the compound of the formula (IA)

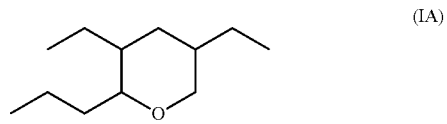

or one or more stereoisomers thereof, where in case that the composition contains the compound of formula (IA) or one or more stereoisomers thereof, this is contained in an amount of at most 30% by weight, preferably at most 20% by weight, relative to the overall weight of compounds of formulae (IA), (IB) and (IE).

6. The aroma chemical composition according to claim 1, selected from the group consisting of perfume compositions, body care compositions, hygiene articles, cleaning compositions, textile detergent compositions, compositions for scent dispensers, foods, food supplements, pharmaceutical compositions and crop protection compositions.

7. The aroma chemical composition according to claim 1, comprising a compound of formula (I) or a mixture of different compounds of formula (I), or a stereoisomer of a compound of formula (I) or a mixture of stereoisomers of a compound of formula (I) or of different compounds of formula (I) in an overall amount of from 0.001 to 99.9% by weight, based on the total weight of the composition.

8. A method for preparing a compound of formula (I), or a stereoisomer thereof, or a mixture of different compounds of formula (I), or a mixture of stereoisomers of a compound of formula (I) or of different compounds of formula (I) according to claim 1, comprising (i) subjecting n-butanal to an aldol condensation reaction;

(ii) subjecting the reaction product of step (i) containing 2-ethylhexenal to catalytic hydrogenation in the presence of a palladium, platinum or ruthenium catalyst;

(iii) removing 2-ethylhexanal formed in step (ii) by distillation; and (iv.1) subjecting the bottom fraction of the distillation in step (iii) to a distillation; and (v.1.1) isolating from the distillation product of step (iv.1) a compound of formula (I) in which $R^1$ and $R^2$, together with the carbon atoms to which they are bound, form a C—C double bond and $R^3$, $R^4$ and $R^5$ are hydrogen; or $R^2$ and $R^3$, together with the carbon atoms to which they are bound, form a C—C double bond and $R^1$, $R^4$ and $R^5$ are hydrogen; or $R^3$ and $R^4$, together with the carbon atoms to which they are bound, form a C—C double bond and $R^1$, $R^2$ and $R^5$ are hydrogen; or $R^4$ and $R^5$, together with the carbon atoms to which they are bound, form a C—C double bond and $R^1$, $R^2$ and $R^3$ are hydrogen; or $R^1$ and $R^2$, together with the carbon atoms to which they are bound, form a C—C double bond, $R^3$ and $R^4$, together with the carbon atoms to which they are bound, form a C—C double bond, and $R^5$ is hydrogen; or $R^1$ and $R^2$, together with the carbon atoms to which they are bound, form a C—C double bond, $R^4$ and $R^5$, together with the carbon atoms to which they are bound, form a C—C double bond, and $R^3$ is hydrogen; or $R^2$ and $R^3$, together with the carbon atoms to which they are bound, form a C—C double bond, $R^4$ and $R^5$, together with the carbon atoms to which they are bound, form a C—C double bond, and $R^1$ is hydrogen; or a mixture containing at least two of these compounds; or a mixture containing at least one of this compounds and a compound (I) in which $R^1$, $R^2$, $R^3$, $R^4$ and $R^5$ are hydrogen; or one or more stereoisomers of the above compounds;

or (v.1.2) subjecting the distillation product of step (iv.1) to catalytic hydrogenation; and (vi.1) isolating the compound of formula (I) in which $R^1$, $R^2$, $R^3$, $R^4$ and $R^5$ are hydrogen or one or more stereoisomers thereof or a mixture containing the compound of formula (I) in which $R^1$, $R^2$, $R^3$, $R^4$ and $R^5$ are hydrogen or one or more stereoisomers thereof;

or (iv.2) subjecting the bottom fraction of the distillation in step (iii) to catalytic hydrogenation; and (v.2) isolating the compound of formula (I) in which $R^1$, $R^2$, $R^3$, $R^4$ and $R^5$ are hydrogen or one or more stereoisomers thereof or a mixture containing the compound of formula (I) in which $R^1$, $R^2$, $R^3$, $R^4$ and $R^5$ are hydrogen or one or more stereoisomers thereof.

9. The method according to claim 8, where step (i) is carried out under basic conditions and at a reaction temperature of at least 40° C.

10. The method according to claim 8, where the catalytic hydrogenation of step (ii) is carried out in the presence of a palladium catalyst.

11. A method for preparing a compound of the formula (I) in which $R^1$, $R^2$, $R^3$, $R^4$ and $R^5$ are hydrogen or a stereoisomer thereof or a mixture of stereoisomers thereof according to claim 1, comprising (a) subjecting n-butanal to an aldol condensation reaction;

(b) subjecting the reaction product of step (a) containing 2-ethylhexenal to catalytic hydrogenation in the presence of a catalyst suitable for reducing both C—C double bonds to C—C single bonds and aldehyde groups to hydroxy groups;

(c) removing 2-ethylhexanol formed in step (b) by distillation;

(d.1) subjecting the bottom fraction of the distillation in step (c) to a distillation;

(e.1) subjecting the distillation product of step (d.1) to reaction conditions suitable for the cyclization of diols; and (f.1) isolating the compound of formula (I) in which $R^1$, $R^2$, $R^3$, $R^4$ and $R^5$ are hydrogen or one or more stereoisomers thereof or a mixture containing the compound of formula (I) in which $R^1$, $R^2$, $R^3$, $R^4$ and $R^5$ are hydrogen or one or more stereoisomers thereof;

or (d.2) subjecting the bottom fraction of the distillation in step (c) to reaction conditions suitable for the cyclization of diols; and (e.2) isolating the compound of formula (I) in which $R^1$, $R^2$, $R^3$, $R^4$ and $R^5$ are hydrogen or one or more stereoisomers thereof or a mixture containing the compound of formula (I) in which $R^1$, $R^2$, $R^3$, $R^4$ and $R^5$ are hydrogen or one or more stereoisomers thereof.

12. The method according to claim 11, where step (a) is carried out under basic conditions and at a reaction temperature of at least 40° C.

13. The method according to any of claim 11, where the catalytic hydrogenation of step (b) is carried out in the presence of a nickel, chromium, copper, zinc, manganese or cobalt catalyst.

14. The method according to claim 11, where the reaction conditions suitable for the cyclization of diols in step (e.1) or (d.2) are acidic conditions using a cation exchanger.

15. An aroma chemical composition comprising one or more compounds of formula (I) or one or more stereoisomers thereof as defined in claim 1.

16. A method for preparing a fragranced composition or for modifying the scent character of a fragranced composition, comprising incorporating the compound of formula (I) or a stereoisomer thereof or a mixture of different compounds of formula (I), or a mixture of stereoisomers of a compound of formula (I) or of different compounds of formula (I) according to claim 1 into said composition.

17. The method according to claim 16, where the composition is selected from the group consisting of perfume compositions, body care compositions, hygiene articles, cleaning compositions, textile detergent compositions, compositions for scent dispensers, food, food supplements, pharmaceutical compositions and crop protection compositions.

18. The aroma chemical composition according to claim 1, comprising
- a compound of formula (I), or a stereoisomer thereof, or a mixture of different compounds of formula (I), or a mixture of stereoisomers of a compound of formula (I) or of different compounds of formula (I); and
- at least one further aroma chemical and/or at least one non-aroma chemical component which is selected from the group consisting of surfactants, oil components and solvents.

* * * * *